(12) United States Patent
Wang et al.

(10) Patent No.: US 8,765,934 B2
(45) Date of Patent: Jul. 1, 2014

(54) METHODS FOR CONJUGATING NUCLEIC ACIDS WITH SMALL MOLECULES

(75) Inventors: Tzu-Pin Wang, Tainan (TW); Yi-Jhang Ciou, Pingtung County (TW)

(73) Assignee: Kaohsiung Medical University, Kaohsiung (TW)

( * ) Notice: Subject to any disclaimer, the term of this patent is extended or adjusted under 35 U.S.C. 154(b) by 153 days.

(21) Appl. No.: 13/188,989

(22) Filed: Jul. 22, 2011

(65) Prior Publication Data
US 2012/0177573 A1 Jul. 12, 2012

(30) Foreign Application Priority Data

Jan. 12, 2011 (TW) .............................. 100101162 A

(51) Int. Cl.
*C07H 21/00* (2006.01)
*C12Q 1/68* (2006.01)
*C07D 293/10* (2006.01)
*C07D 235/02* (2006.01)

(52) U.S. Cl.
USPC ......... 536/25.32; 435/6.1; 548/100; 548/120; 548/303.7

(58) Field of Classification Search
USPC ................. 435/6.1; 536/25.32; 548/100, 120, 548/303.7
See application file for complete search history.

(56) References Cited

U.S. PATENT DOCUMENTS

2011/0137023 A1 6/2011 Meier et al.
2012/0116067 A1 5/2012 Meier et al.

FOREIGN PATENT DOCUMENTS

WO 2010/015245 2/2010
WO 2010/127666 11/2010

OTHER PUBLICATIONS

Office Action, Taiwan Patent Application No. 201229511 (Issued Feb. 22, 2013).

*Primary Examiner* — Jezia Riley
(74) *Attorney, Agent, or Firm* — Volpe and Koeing, P.C.

(57) ABSTRACT

A method for conjugating a nucleic acid with a molecule is provided. The method includes steps of (a) reacting the nucleic acid having a 5'-monophosphate with an activating agent in a first buffer to form a solution; (b) mixing an alcohol with the solution formed in the step (a) to obtain an intermediate; and (c) dissolving the intermediate in a second buffer containing an ethylenediaminetetraacetic acid (EDTA) and adding a nucleophile thereto to react the intermediate with the nucleophile.

9 Claims, 15 Drawing Sheets

METHODS FOR CONJUGATING NUCLEIC ACIDS WITH SMALL MOLECULES

CROSS-REFERENCES TO RELATED APPLICATIONS AND CLAIMS OF PRIORITY

The application claims the benefit of Taiwan Patent Application No. 100101162, filed on Jan. 12, 2011, in the Taiwan Intellectual Property Office, the disclosures of which are incorporated herein in their entirety by reference.

FIELD OF THE INVENTION

The present invention relates to a method for conjugating nucleic acids with small molecules, and more particularly to a method for conjugating nucleic acids with peptides.

BACKGROUND OF THE INVENTION

Covalent modifications of nucleic acids have been used to explore the diverse functions of nucleic acids and to characterize their intrinsic biochemical properties in biological systems. Continuous development of covalent conjugation methods for nucleic acids further facilitates applications of nucleic acids as research tools for chemical and biomedical studies, improves potency, and promotes specificity of nucleic acids as therapeutic reagents in medicine. Oligonucleotides conjugated with peptides to afford peptide-oligonucleotide conjugates (POCs) hold promise as an effective therapeutic reagent to treat viral infections and genetic diseases. Applications of POCs in basic and clinical research have produced nucleic acids with improved biological stability, cellular uptake efficiency, and in vivo cell-specific targeting.

Preparation of POCs is essential for therapeutic applications of nucleic acids such as oligonucleotides. The direct use of oligonucleotides in medicine generally falls short of disease treatment expectations due to poor cell specificity and uptake of nucleic acids, and inaccessibility of nucleic acids to cell nuclei. The conjugation of oligonucleotides with peptides is thus the most common approach to circumvent cell delivery and specificity problems of oligonucleotides. However, methods currently available to prepare POCs are inefficient and inconvenient for typical research laboratories. The difficulties experienced when preparing desired effective POCs restrict the broad applications of POCs in achieving their much-needed medical applications. POCs are generally prepared by post solid-phase synthesis to couple peptides with oligonucleotides (fragment coupling strategy) or stepwise solid-phase synthesis. The generic fragment coupling strategy separately synthesizes peptides and oligonucleotides by standard solid-phase synthesis protocols, and then both are covalently linked together by post solid-phase synthesis. There are limited reactions available for POC formation because peptides primarily use unstable phosphodiester linkages when conjugating to 5'- or 3'-termini or ester linkages when linking to 2'-positions of riboses in oligonucleotides. The development of a facile approach to use hydroxyl or phosphate groups in standard oligonucleotides to afford stable POCs with high purity and yields is highly desirable.

In order to overcome the drawbacks in the prior art, a method for conjugating nucleic acids with small molecules is provided. The particular design in the present invention not only solves the problems described above, but also is easy to be implemented. Thus, the present invention has potential use in the industries.

SUMMARY OF THE INVENTION

In accordance with one aspect of the present invention, a method for conjugating nucleic acids with other molecules is provided. The method includes steps of (a) reacting the nucleic acid having a 5'-monophosphate with an activating agent in a first buffer to form a solution; (b) mixing an alcohol with the solution formed in the step (a) to obtain an intermediate; and (c) dissolving the intermediate in a second buffer containing an ethylenediaminetetraacetic acid (EDTA) and adding a nucleophile thereinto to react the intermediate with the nucleophile.

In accordance with another aspect of the present invention, a method for conjugating nucleic acids with other molecules is provided. The method includes steps of (a) reacting the nucleic acid having a 5'-monophosphate with an activating agent in a first buffer to form a solution; and (b) adding a second buffer containing an ethylenediaminetetraacetic acid (EDTA) and a nucleophile into the solution.

In accordance with a further aspect of the present invention, a process is provided. The process is one selected from a group consisting of RNA interference, gene silencing, gene therapy, nucleic acid/protein quantification and detection of in vivo protein-nucleic acid interaction, performed by using the method described above.

In accordance with further another aspect of the present invention, a compound is provided. The compound has a structure of

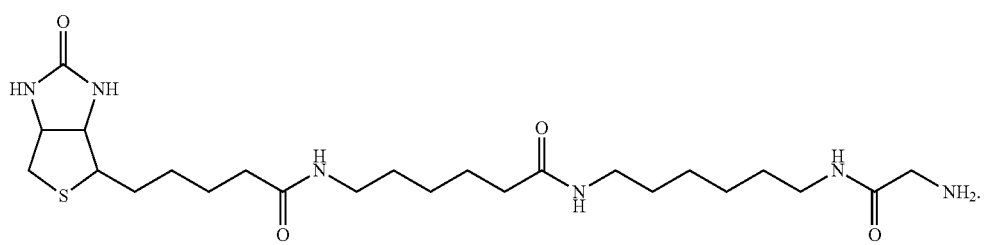

The above objects and advantages of the present invention will become more readily apparent to those ordinarily skilled in the art after reviewing the following detailed descriptions and accompanying drawings, in which:

BRIEF DESCRIPTION OF THE DRAWINGS

FIGS. 3(A)~3(B) show phosphoramidation reactions of the $^{32}$P-labeled GMP-primed TW17 RNA with 11, wherein FIG. 3(A) shows results from the one-step phosphoramidation reaction, and FIG. 3(B) shows results from the two-step phosphoramidation reaction;

FIGS. 4(A)~4(B) show the one-step phosphoramidation reactions for the conjugations of the $^{32}$P-labeled DNA with 11, wherein FIG. 4(A) shows 8% urea PAGE for the double-stranded DNA (the TW 17 DNA) conjugations, and FIG. 4(B) shows 20% urea PAGE for the single-stranded DNA (the 3'-primer) conjugations;

FIGS. 5(A)~5(B) show the two-step phosphoramidation reactions for the conjugations of the $^{32}$P-labeled DNA with 11, wherein FIG. 5(A) shows 8% urea PAGE for the double-stranded DNA (the TW17 DNA) conjugations, and FIG. 5(B) shows 20% urea PAGE for the single-stranded DNA (the 3'-primer) conjugations;

FIGS. 6(A)~6(C) show the phosphoramidation reactions of the $^{32}$P-labeled DNA or RNA with 1,6-hexanediamine, wherein FIG. 6(A) is for the GMP-primed TW17 RNA conjugations, FIG. 6(B) is for the doubled-stranded TW17 DNA conjugations, and FIG. 6(C) is for the single-stranded 3'-primer DNA conjugations;

FIGS. 7(A)~7(D) show the result of preparation of the nucleic acid-BSA conjugates, wherein the $^{32}$P-labeled GMP-primed TW17 RNA was conjugated with 1,6-hexanediamine using the one-step phosphoramidation reaction described above, followed by reactions with DSS or DSG and finally coupled with BSA, wherein FIG. 7(A) shows the result in the absence of 3 M NaCl and FIG. 7(B) shows the result in the presence of 3 M NaCl, and the double-stranded TW17 DNA-BSA conjugates are coupled, wherein FIG. 7(C) shows the result in the absence of 3 M NaCl and FIG. 7(D) shows the result in the presence of 3 M NaCl;

FIGS. 8(A)~8(B) show the result of phosphoramidation-prepared 3'-primer DNA applied to PCR reactions, wherein FIG. 8(A) shows the result of using 3'-primer DNA-11 conjugate, and FIG. 8(B) shows the result of using 3'-primer DNA-fluorescein conjugate;

FIGS. 9(A)~9(C) show the phosphoramidation reactions of the $^{32}$P-labeled DNA or RNA with tetraglycine (18) to prepare nucleic acid-tetraglycine conjugates, wherein FIG. 9(A) is for the GMP-primed TW17 RNA conjugations, FIG. 9(B) is for the doubled-stranded TW17 DNA conjugations, and FIG. 9(C) is for the single-stranded 3'-primer DNA conjugations; and FIGS. 10(A)~10(D) show the effects of the types and concentrations of surfactants on the yields of two-step phosphoramidation reactions, wherein FIG. 10(A) shows the effect under a 15% surfactant, FIG. 10(B) shows the effect under a 20% surfactant, FIG. 10(C) shows the effect under a 25% surfactant, and FIG. 10(D) shows the effect under a 32% surfactant.

DETAILED DESCRIPTION OF THE PREFERRED EMBODIMENT

Figure 1:
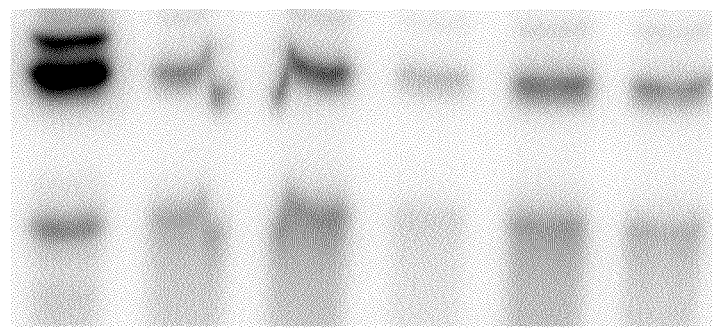
FIGS. 1(A)~1(F) show the results of optimization of phosphoramidation reactions.
Figure 1:
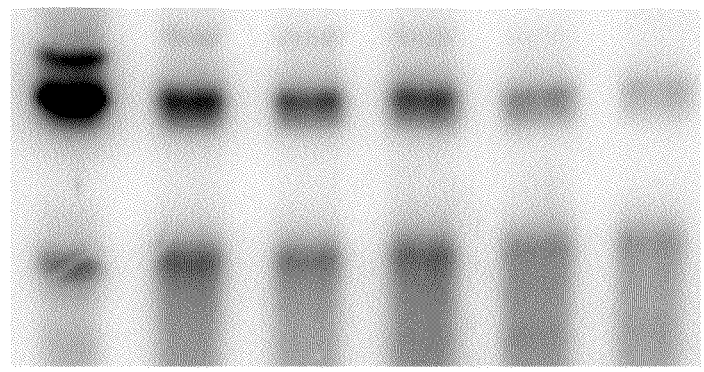
Figure 1:
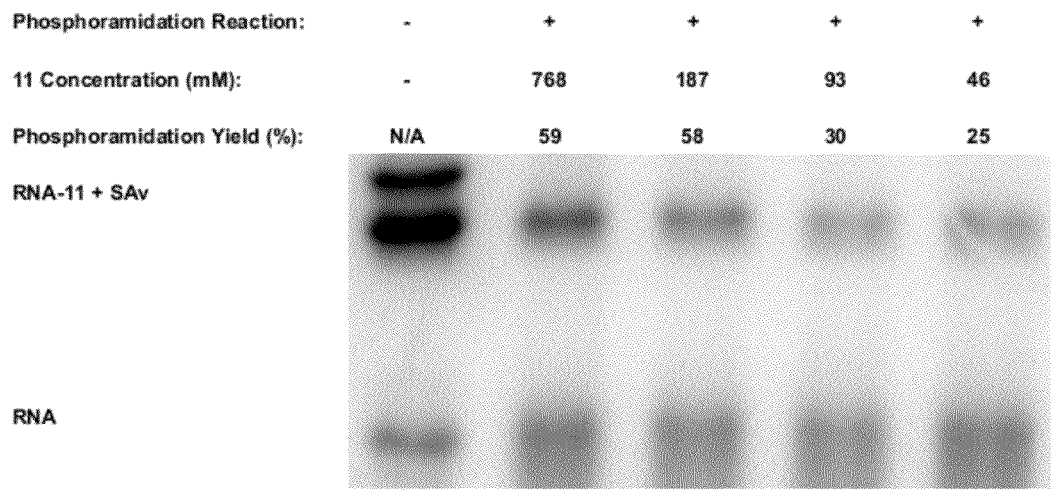
Figure 1:
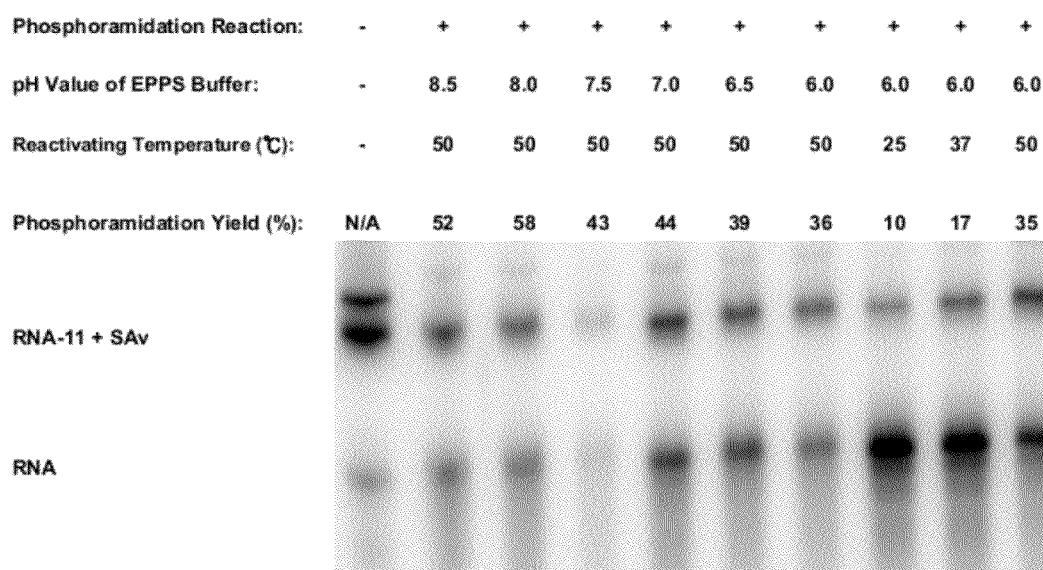
Figure 1:
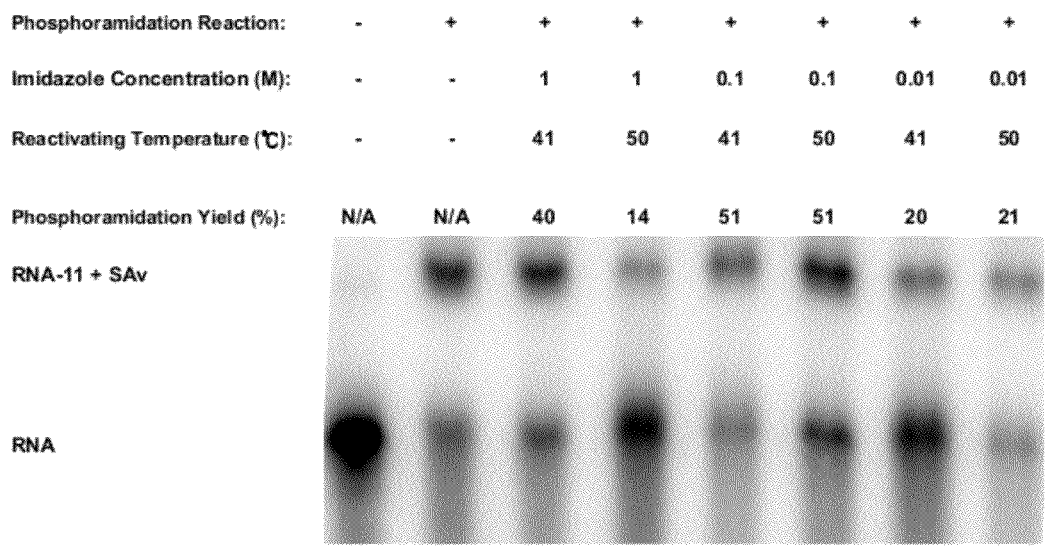
Figure 1:
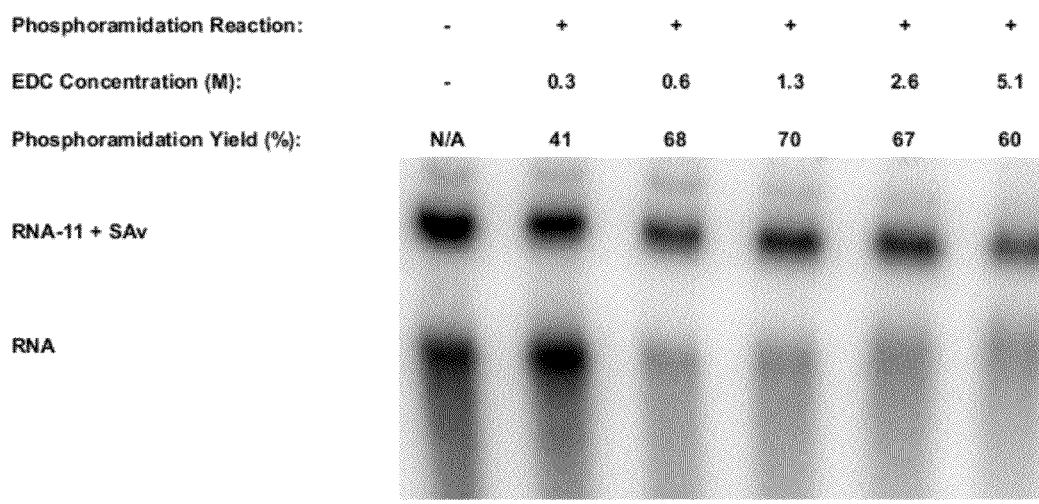

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed.

Synthesis of the Biotin Derivative (11)

The synthesis of 11 is shown in Scheme 1 as follows.

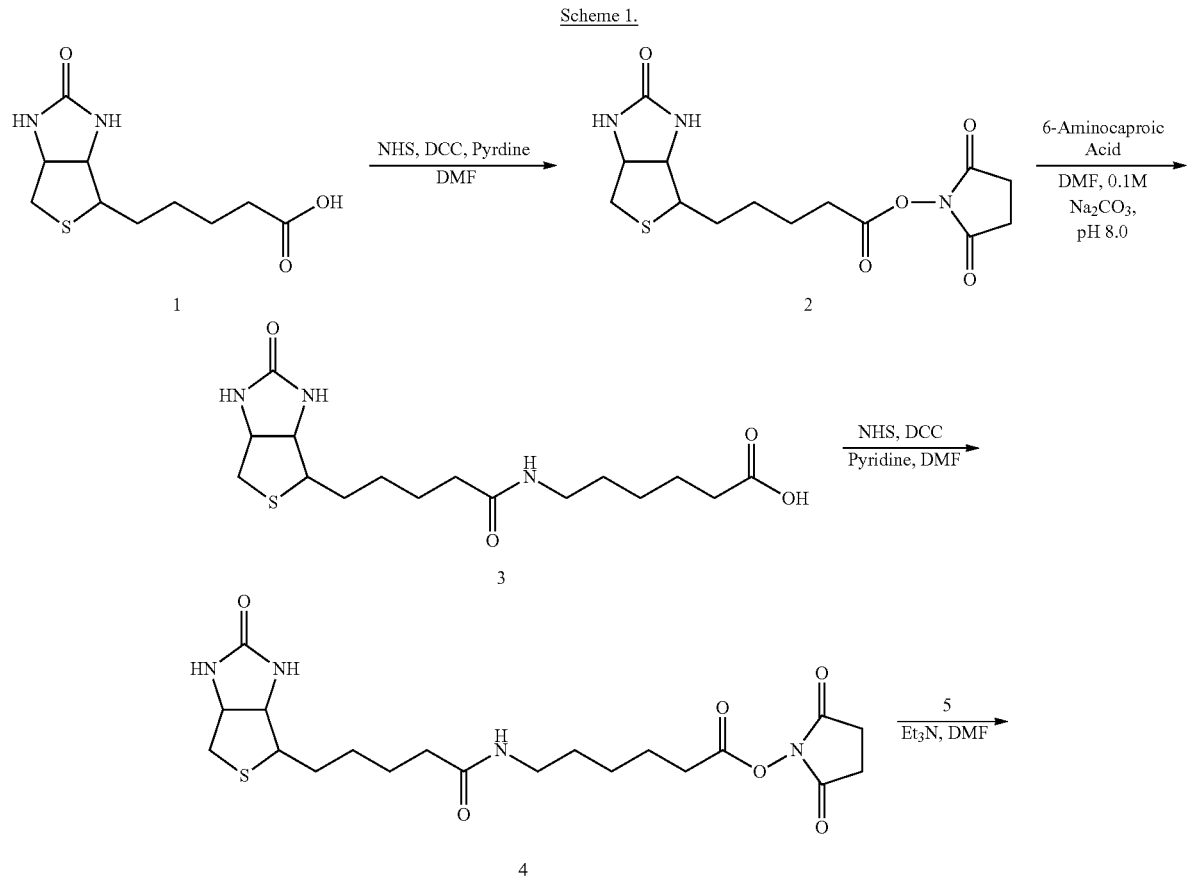

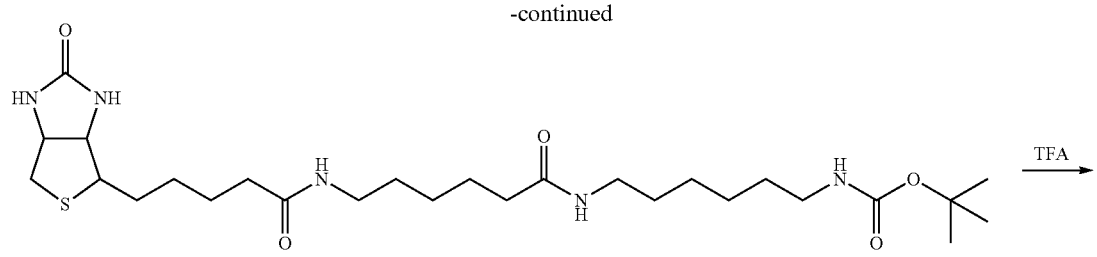

6

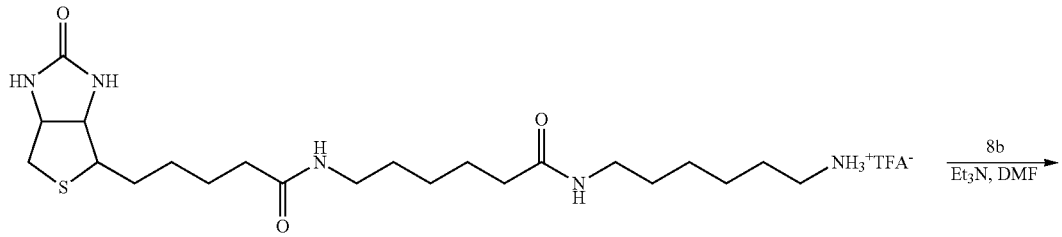

7

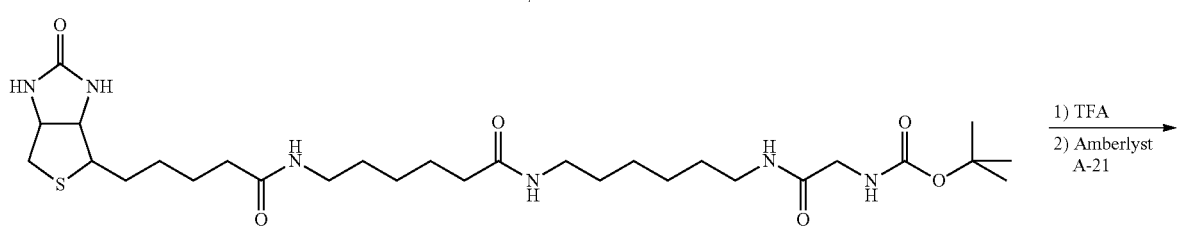

9

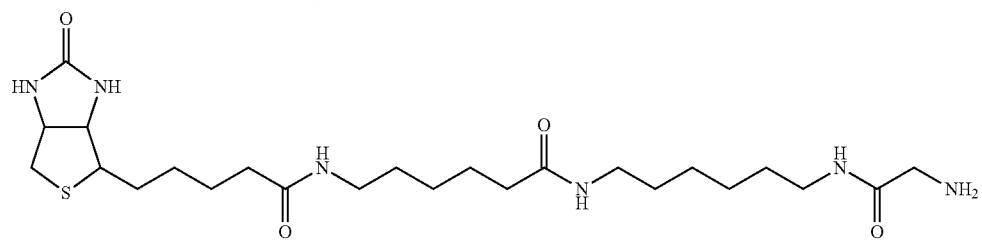

11

5-(2-Oxo-hexahydrothieno[3,4-d]imidazol-4-yl)-pentanoic Acid 2,5-Dioxo-pyrrolidin-1-yl Ester (2)

The method for synthesis of 2 was modified from that of Bayer and Wilchek. In brief, biotin (1; 0.31 g, 1.26 mmol) was completely dissolved in DMF (9 mL) with gentle warming. After cooling the 1 solution to room temperature without reprecipitation, it was added to N,N'-dicyclohexylcarbodiimide (DCC; 0.26 g, 1.28 mmol) and pyridine (0.10 mL, 1.26 mmol) while stirring for 5 min at room temperature, followed by the addition of N-hydroxysuccinimide (NHS; 0.19 g, 1.65 mmol) with continuous stirring for 24 h. The reaction product was filtered and concentrated under reduced pressure. The obtained solid was redissolved in 2-propanol (50 mL) with gentle heating, cooled down to room temperature, and reprecipitated at 4° C. overnight. The product was scraped out of the glassware, washed with cold 2-propanol, and air dried to give 2 as white solid (0.36 g; 82.4%). $^1$H NMR (400 MHz) (DMSO) δ: 6.46 (s, 1H, CONH), 6.39 (s, 1H, CONH), 4.31 (t, 1H, CHN), 4.16 (t, 1H, CHN), 3.12 (dd, 1H, CHS), 2.83 (s, 4H, CH$_2$ of NHS), 2.71 (d, 1H, CHHS), 2.69 (t, 2H, CH$_2$CO), 2.59 (d, 1H, CHHS), 1.43-1.68 (m, 6H). $^{13}$C NMR (100.67 MHz) (DMSO) δ: 170.42, 162.85, 61.01, 59.28, 55.33, 30.08, 27.91, 27.68, 25.51. HRMS (ESI) calculated for $C_{14}H_{19}N_3O_5S$, [M+Na]$^+$ 364.0943 (calcd.), 364.0940 (found).

6-[5-(2-Oxo-hexahydro-thieno[3,4-d]imidazol-4-yl)-pentanoylamino]-hexanoic Acid (3)

5-(2-Oxo-hexahydro-thieno[3,4-d]imidazol-4-yl)-pentanoic acid 2,5-dioxo-pyrrolidin-1-yl ester (2; 0.35 g, 1.03 mmol) was completely dissolved in DMF (3 mL) with gentle warming. After cooling the 2 solution to room temperature without reprecipitation, it was mixed with a solution of ε-aminocaproic acid (0.18 g, 1.37 mmol) in sodium bicarbonate buffer (0.1 M, pH 8.0; 4 mL) while stirring. After 4 h at room temperature, the reaction mixture was acidified by HCl solution (1 N) to assist in the formation of white precipitate. The white solid was washed with cold HCl solution, dried over ether, and air-dried to afford 3 (0.30 g; 80.5%). $^1$H NMR (400 MHz) (DMSO) δ: 7.78 (s, 1H, CONH), 6.46 (s, 1H, CONH), 6.38 (s, 1H, CONH), 4.32 (t, 1H, CHN), 4.14 (t, 1H, CHN), 3.11 (dd, 1H, CHS), 3.02 (t, 2H, CH$_2$NH), 2.84 (d, 1H, CHHS), 2.59 (d, 1H, CHHS), 2.18 (t, 2H, CH$_2$COOH), 2.05 (t, 2H, CH$_2$CO), 1.23-1.68 (m, 12H). $^{13}$C NMR (100.67 MHz) (DMSO) δ: 174.45, 171.79, 162.70, 61.03, 59.18, 55.43, 35.21, 33.60, 28.90, 28.02, 25.97, 25.33, 24.22.

HRMS (ESI) calculated for $C_{16}H_{27}N_3O_4S$, $[M+Na]^+$ 380.1620 (calcd.), 380.1617 (found).

6-[5-(2-Oxo-hexahydro-thieno[3,4-d]imidazol-4-yl)-pentanoylamino]-hexanoic Acid 2,5-Dioxo-pyrrolidin-1-yl Ester (4)

Synthesis of 4 with high purity was achieved following the method of Wilchek and Bayer with critical changes in workup procedures. 6-[5-(2-Oxo-hexahydro-thieno[3,4-d]imidazol-4-yl)-pentanoylamino]-hexanoic acid (3; 0.31 g, 0.87 mmol) was completely dissolved in DMF (20 mL) with gentle warming. After cooling the 3 solution to room temperature without reprecipitation, DCC (0.34 g, 1.65 mmol) and pyridine (0.07 mL, 0.83 mmol) were added to the solution while stirring for 5 min, followed by the addition of NHS (0.16 g, 1.46 mmol) with continuous stirring for 18 h. The reaction product was filtered and concentrated under reduced pressure. The remaining solid was redissolved in 2-propanol (40 mL) with gentle heating, cooled down to room temperature, and reprecipitated at 4° C. overnight. The product was scraped out of the glassware, washed with cold 2-propanol, and air-dried to obtain 4 (0.22 g; 56.8%) as a white solid. $^1$H NMR (400 MHz) (DMSO) δ: 7.77 (s, $^1$H, CONH), 6.45 (s, 1H, CONH), 6.38 (s, 1H, CONH), 4.31 (t, 1H, CHN), 4.15 (t, 1H, CHN), 3.11 (dd, 1H, CHS), 3.03 (t, 2H, $CH_2NH$), 2.83 (s, 4H, $CH_2$ of NHS), 2.79 (d, 1H, CHHS), 2.67 (t, 2H, $CH_2COOH$), 2.60 (d, 1H, CHHS), 2.06 (t, 2H, $CH_2CO$), 1.04-1.75 (m, 12H). $^{13}$C NMR (100.67 MHz) (DMSO) δ: 171.90, 170.36, 169.03, 162.79, 61.13, 59.27, 55.53, 38.14, 35.32, 30.24, 28.74, 28.32, 28.14, 25.54, 25.41, 24.05. HRMS (ESI) calculated for $C_{20}H_{30}N_4O_6S$, $[M+Na]^+$ 477.1784 (calcd.), 477.1784 (found).

(6-Amino-hexyl)-carbamic Acid tert-Butyl Ester (5)

1,6-Hexanediamine (1.0 g, 8.61 mmol) was completely dissolved in dichloromethane (DCM; 7 mL). The solution was chilled to 0° C., followed by the addition of di-tert-butyl dicarbonate (0.63 g, 2.87 mmol) with stirring. The reaction was allowed to proceed at room temperature overnight. The acquired reaction product was diluted with chloroform (7.5 mL), extracted with 5% $Na_2CO_3$ twice, and its organic phase concentrated under reduced pressure. The obtained solid was dissolved in 1 N HCl and extracted with ether twice. The pH of the acquired aqueous phase was adjusted to 10 with NaOH and extracted with ethyl acetate (EA) five times. The final organic phase was dried over $MgSO_4$ and concentrated under reduced pressure to give oil-like 5 (0.25 g; 39.8%). $^1$H NMR (400 MHz) ($CDCl_3$) δ: 4.54 (s, 1H, CONH), 3.11 (t, 2H, $CH_2NH$), 2.68 (t, 2H, $CH_2NH_2$), 1.40-1.50 (s, 9H, $CH_3$; m, 4H, $CH_2$), 1.25-1.37 (m, 4H, $CH_2$). $^{13}$C NMR (100.67 MHz) (DMSO) δ: 77.00, 41.98, 33.55, 29.95, 28.33, 26.48. HRMS (ESI) calculated for $C_{11}H_{24}N_2O_2$, $[M+H]^+$ 217.1916 (calcd.), 217.1917 (found).

(6-{6-[5-(2-Oxo-hexahydro-thieno[3,4-d]imidazol-4-yl)-pentanoylamino]-hexanoylamino}-hexyl)-carbamic Acid tert-Butyl Ester (6)

6-[5-(2-Oxo-hexahydro-thieno[3,4-d]imidazol-4-yl)-pentanoylamino]-hexanoic acid 2,5-dioxo-pyrrolidin-1-yl ester (4; 0.39 g, 0.86 mmol) was completely dissolved in DMF (15 mL) with gentle warming. After cooling the solution to room temperature without reprecipitation, it was mixed with triethylamine ($Et_3N$; 0.52 g, 5.15 mmol) followed by the addition of 5 (0.25 g, 1.14 mmol) in DMF (3 mL) dropwise while stirring. After overnight reaction at room temperature, the mixture was filtered, evaporated in vacuo, and loaded to a silica column for further purification. The products were separated by eluting with mobile phases of 5-20% MeOH in DCM to afford 6 (0.45 g; 93.8%) as a yellowish solid. $^1$H NMR (400 MHz) ($CD_3OD$) δ: 4.53 (t, 1H, CHN), 4.34 (t, 1H, CHN), 3.25 (dd, 1H, CHS), 3.20 (t, 2H, $CH_2NH$), 3.08 (t, 2H, $CH_2NH$), 2.96 (d, 1H, CHHS), 2.73 (d, 1H, CHHS), 2.22 (t, 4H, $CH_2CO$), 1.38-1.80 (m, 29H). $^{13}$C NMR (100.67 MHz) (DMSO) δ: 176.02, 175.97, 166.05, 158.50, 79.50, 63.39, 61.63, 57.01, 41.24, 41.04, 40.24, 36.99, 36.82, 30.90, 30.35, 30.13, 29.78, 29.49, 28.80, 27.56, 26.92, 26.74. HRMS (ESI) calculated for $C_{27}H_{49}N_5O_5S$, $[M+Na]^+$ 578.3352 (calcd.), 578.3349 (found).

6-[5-(2-Oxo-hexahydro-thieno[3,4-d]imidazol-4-yl)-pentanoylamino]-hexanoic Acid (6-amino-hexyl)-amide, TFA Salt (7)

(6-{6-[5-(2-Oxo-hexahydro-thieno[3,4-d]imidazol-4-yl)-pentanoylamino]-hexanoylamino}-hexyl)-carbamic acid tert-butyl ester (6; 0.23 g, 0.39 mmol) was dissolved in trifluoroacetic acid (TFA) and stirred at room temperature for 45 min. The product was concentrated under reduced pressure, washed by ether, and again concentrated under reduced pressure to obtain oil-like 7 (0.22 g; 100%) as TFA salts. $^1$H NMR (400 MHz) ($CD_3OD$) δ: 4.58 (t, 1H, CHN), 4.35 (t, 1H, CHN), 3.25 (dd, 1H, CHS), 3.21 (t, 4H, $CH_2NH$), 2.96 (d, 1H, CHHS), 2.95 (t, 2H, $CH_2NH_3^+$), 2.75 (d, 1H, CHHS), 1.22-1.80 (m, 20H). $^{13}$C NMR (100.67 MHz) (DMSO) δ: 176.67, 166.14, 63.38, 61.63, 57.03, 41.05, 40.64, 40.19, 40.01, 36.98, 36.81, 30.17, 29.78, 29.50, 28.50, 27.53, 27.33, 26.96, 26.72, 26.27. HRMS (ESI) calculated for $C_{22}H_{41}N_5O_3S$, $[M+H]^+$ 456.3008 (calcd.), 456.3009 (found).

Carbamoylmethyl-Carbamic Acid Tert-Butyl Ester (8a)

Glycine (0.45 g, 6.05 mmol) was dissolved in 6 mL of dioxane/water mixture (dioxane:water=4:2) with stirring, followed by the addition of 1 N NaOH (2 mL). The acquired glycine solution was immersed in an ice-water bath and mixed with di-tert-butyl dicarbonate (1.38 g, 6.31 mmol) dropwise while stirring to initiate the reaction. The reaction was allowed to proceed at room temperature overnight. The reaction was diluted with water (2 mL) and EA (10 mL), extracted with 1 N HCl twice, and extracted with water twice. The final organic phase was dried over $MgSO_4$ and evaporated under reduced pressure to give oil-like 8a (0.94 g; 90%). $^1$H NMR (400 MHz) ($CDCl_3$) δ: 5.42 (s, 1H, CONH), 3.91 (d, 2H, $CH_2CO$), 1.44 (s, 9H, $CCH_3$). $^{13}$C NMR (100.67 MHz) ($CDCl_3$) δ: 177.0, 156.0, 79.6, 35.8, 34.3, 28.2.

tert-Butoxycarbonylamino-acetic Acid 2,5-Dioxo-pyrrolidin-1-yl Ester (8b)

Carbamoylmethyl-carbamic acid tert-butyl ester (8a; 0.61 g, 3.48 mmol) and NHS (0.61 g, 5.34 mmol) were dissolved in THF (7 mL), followed by dropwise addition of DCC (1.42 g, 6.9 mmol) in THF (7 mL) with stirring. After overnight reaction at room temperature, the mixture was quenched by the addition of three drops of glacial acetic acid, stirred for 1 h, and filtered to remove suspension. The acquired filtrate was concentrated under reduced pressure, resuspended in 2-propanol (25 mL) while stirring for 1 h, and filtered to separate the suspension from its filtrate. The remaining solid was washed by 2-propanol and dried to afford white-colored 8b (0.62 g; 68.8%). $^1$H NMR (400 MHz) ($CDCl_3$) δ: 5.00 (s, 1H, CONH), 4.27 (d, 2H, $CH_2CO$), 2.85 (s, 4H, $CNOCH_2CH_2$), 1.43 (s, 9H, $CCH_3$). $^{13}$C NMR (100.67 MHz) ($CDCl_3$) δ: 168.6 (CONH), 77.0 ($CH_2N$), 40.2 ($CH_2CO$), 37.4 ($CH_2CO$), 25.5 ($CH_3CO$).

[(6-{6-[5-(2-Oxo-hexahydro-thieno[3,4-d]imidazol-4-yl)-pentanoylamino]-hexanoylamino}-hexylcarbamoyl)-methyl]-carbamic Acid tert-Butyl Ester (9)

Tert-Butoxycarbonylamino-acetic acid 2,5-dioxo-pyrrolidin-1-yl ester (8b; 0.18 g, 0.69 mmol) dissolved in DMF (5 mL) was added slowly to a DMF solution (3 mL) containing 6-[5-(2-oxo-hexahydro-thieno[3,4-d]imidazol-4-yl)-pentanoylamino]-hexanoic acid (6-amino-hexyl)-amide (7; 0.16 g, 0.27 mmol) and Et$_3$N (0.1 mL, 0.72 mmol) while stirring at room temperature. The reaction was stopped after 3 h by evaporating DMF in vacuo, and the remaining residue was redissolved in a limited volume of a DCM/MeOH (19:1) solution and loaded to a preequilibrated silica column. The products were separated by eluting with mobile phases of 1-6.67% MeOH in DCM to afford 9 (0.10 g; 62.2%) as a yellow solid. $^1$H NMR (400 MHz) (CD$_3$OD) δ: 4.30 dd, 1H, CHN), 4.15 (dd, 1H, CHN), 3.94 (d, 2H, CH$_2$CO), 3.32 (quin, 4H, CH$_2$NH), 2.99 (q, 2H, CH$_2$N), 2.92 (d, 1H, CHHS), 2.75 (d, 1H, CHHS), 2.20 (t, 4H, CH$_2$CO), 1.44-1.88 (m, 29H). $^{13}$C NMR (100.67 MHz) (CD$_3$OD) δ: 175.9 (CO), 63.7 (CHN), 61.6 (CHN), 56.9 (CHS), 49.0 (CH$_2$N), 41.0 (CH$_2$CO), 40.2 (CH$_2$N), 36.9 (CH$_2$S), 30.1 (CH$_2$CO), 28.6 (CH$_3$CO), 26.7 (CH$_2$CH$_2$). HRMS (ESI) calculated for C$_{29}$H$_{52}$N$_6$O$_6$S, [M+Na]$^+$ 635.3567 (calcd.), 635.3564 (found).

6-[5-(2-Oxo-hexahydro-thieno[3,4-d]imidazol-4-yl)-pentanoylamino]-hexanoic Acid [6-(2-Amino-acetylamino)-hexyl]-amide, TFA Salt (10)

[(6-{6-[5-(2-Oxo-hexahydro-thieno[3,4-d]imidazol-4-yl)-pentanoylamino]-hexanoylamino}-hexylcarbamoyl)-methyl]carbamic acid tert-butyl ester (9; 0.38 mg, 0.62 mmol) was dissolved in TFA (3 mL) and stirred for 45 min. The product was evaporated under reduced pressure, washed by chloroform, and again concentrated under reduced pressure to remove chloroform and to obtain brown oil-like 10 (0.32 g, 100%). $^1$H NMR (400 MHz) (CD3OD) δ: 4.50 (dd, 1H, CHN), 4.30 (dd, 1H, CHN), 3.64 (s, 2H, CH$_2$CO), 3.13-3.23 (m, 4H, CH$_2$NH), 2.99 (q, 2H, CH$_2$N), 2.93 (dd, 1H, CHHS), 2.72 (d, 1H, CHHS), 2.20 (t, 4H, CH$_2$CO), 1.29-1.88 (m, 20H). $^{13}$C NMR (100.67 MHz) (CD$_3$OD) δ: 175.9 (CO), 63.7 (CHN), 61.6 (CHN), 56.9 (CHS), 49.0 (CH$_2$N), 41.0 (CH$_2$CO), 40.2 (CH$_2$N), 36.9 (CH$_2$S), 30.1 (CH$_2$CO), 26.7 (CH$_2$CH$_2$). HRMS (ESI) calculated for C$_{24}$H$_{44}$N$_6$O$_4$S, [M+H]$^+$ 513.3223 (calcd.), 513.3226 (found).

6-[5-(2-Oxo-hexahydro-thieno[3,4-d]imidazol-4-yl)-pentanoylamino]-hexanoic Acid [6-(2-Amino-acetylamino)-hexyl]-amide (11)

The TFA salt of 6-[5-(2-oxo-hexahydro-thieno[3,4-d]imidazol-4-yl)-pentanoylamino]-hexanoic acid [6-(2-amino-acetylamino)-hexyl]-amide, TFA salt (10; 0.52 g, 0.88 mmol) was dissolved in 5 mL of DCM/MeOH mixture (DCM:MeOH=1:1) and mixed with 10 equiv of Amberlyst A-21 (1.1 mg, 8.8 mmol) while shaking for 30 min. After filtering to remove Amberlyst A-21, the filtrate of the reaction products was concentrated under reduced pressure to afford yellow oil-like 11 (0.42 mg, 93.8%). $^1$H NMR (400 MHz) (CD$_3$OD) δ: 4.49 (dd, 1H, CHN), 4.30 (dd, 1H, CHN), 3.32 (s, 2H, CH$_2$CO), 3.14-3.29 (m, 4H, CH$_2$N), 2.99 (q, 2H, CH$_2$N), 2.86 (s, 1H, CHS), 2.72 (d, 1H, CHS), 2.20 (q, 4H, CH$_2$CO), 1.29-1.88 (m, 20H). $^{13}$C NMR (100.67 MHz) (CD$_3$OD) δ: 175.9 (CO), 63.7 (CHN), 61.6 (CHN), 56.9 (CHS), 49.0 (CH$_2$N), 41.0 (CH$_2$CO), 40.2 (CH$_2$N), 36.9 (CH$_2$S), 30.1 (CH$_2$CO), 26.7 (CH$_2$CH$_2$). HRMS (ESI) calculated for C$_{24}$H$_{44}$N$_6$O$_4$S, [M+H]$^+$ 513.3223 (calcd.), 513.3226 (found).

Synthesis of Tetraglycine (18)

The synthesis of 18 is shown in Scheme 2 as follows.

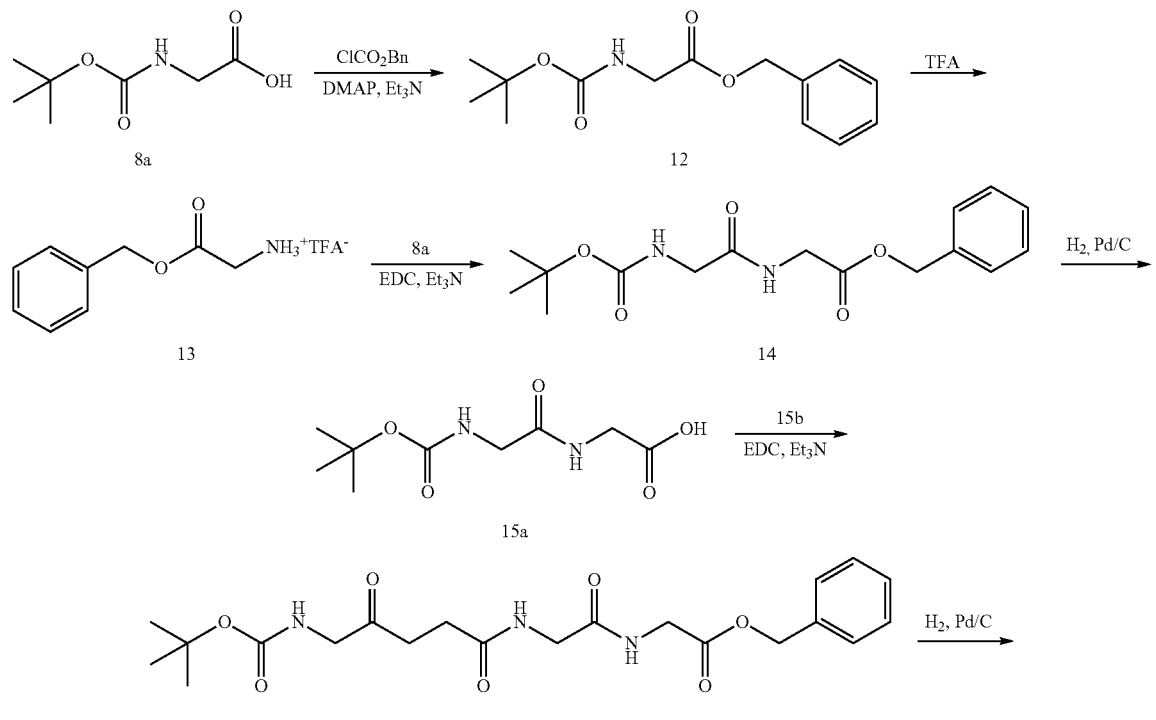

Scheme 2.

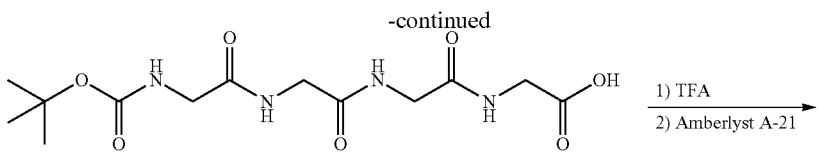

17

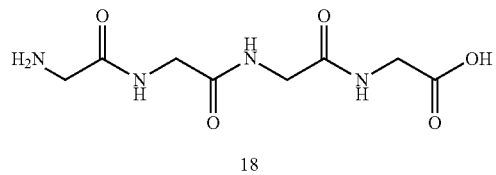

18

Benzyl-2-(tert-butoxycarbonyl)-acetate (12)

Carbamoylmethyl-carbamic acid tert-butyl ester (8a; 0.84 g, 4.8 mmol) was dissolved in dichloromethane (10 mL), and added with triethylamine (1.0 mL, 7.2 mmol) and benzyl chloroformate (0.85 g, 0.75 mL, 5.0 mmol) at 0° C. After stirring for 5 min, 4-dimethylaminopyridine (DMAP; 0.32 g, 2.6 mmol) was added slowly with continuous stirring at 0° C. for 1 h. After the reaction is completed, dichloromethane (10 mL) and saturated $Na_2CO_3$ solution (10 mL) were added. The organic phase was washed by $H_2O$ (10 mL), 1N HCl (20 mL), $H_2O$ (20 mL) and saturated NaCl solution (20 mL) separately, and dried over $MgSO_4$ and concentrated under reduced pressure to remove dichloromethane to obtain white solid product 12 (1.15 g; 95%). $^1$H-NMR (200 MHz) ($CDCl_3$) δ: 7.30~7.38 (m, 5H, ArH), 5.17 (s, 2H, $CO_2CH_2Ph$), 5.02 (br, s, 1H, NHBOC), 3.94 (d, 2H, Gly-H), 1.43 [s, 9H, $CO_2C(CH_3)_3$]

Benzyl-2-aminoacetate, TFA salt (13)

Benzyl-2-(tert-butoxycarbonyl)-acetate (12; 1.29 g, 5.12 mmol) was dissolved in dichloromethane/trifluoroacetic acid mixture (6 ml; dichloromethane:trifluoroacetic acid=1:1) with stirring at 0° C. for 1 h reaction, followed by continuous stirring for 1 h at room temperature. After the reaction was completed, dichloromethane/trifluoroacetic acid mixture was removed by concentration under reduced pressure to give brown oil-like 13 (1.73 g; 100%). $^1$H-NMR (200 MHz) (DMSO) δ: 8.61 (br, s, 3H, $NH_3^+$), 7.32-7.46 (m, 5H, ArH), 5.25 (s, 2H, $CO_2CH_2Ph$), 3.87 (br, s, 2H).

Benzyl-2-[2-(tert-butoxycarbonyl)-acetamido]acetate (14)

Benzyl-2-aminoacetate, TFA salt (13; 1.72 g, 5.12 mmol) and carbamoylmethyl-carbamic acid tert-butyl ester (8a; 1.13 g, 6.19 mmol) were dissolved in 40 mL dichloromethane with stirring at 0° C., followed by addition of N-(3-dimethylaminopropyl)-N-ethylcarbodiimide hydrochloride (EDC; 1.33 g, 7.0 mmol) and triethylamine (1.0 mL, 7.2 mmol), and the reaction was replaced under room temperature with continuous stirring for 6 h. After the reaction was completed, dichloromethane was removed by concentration under reduced pressure. The obtained solid was dissolved in ethyl acetate (50 mL), and then the organic phase was washed by $H_2O$, 5% citric acid, $H_2O$, saturated $NaHCO_3$ and saturated NaCl solution separately, and dried over $MgSO_4$ and concentrated under reduced pressure to remove ethyl acetate to obtain colorless oil-like 14 (1.15 g; 72.6%). $^1$H-NMR (200 MHz) ($CDCl_3$) δ: 7.28-7.33 (m, 5H, ArH), 6.89 (br, s, 1H, $CONHCH_2$), 5.36 (br, s, 1H, NHBOC), 5.13 (s, 2H, $CO_2CH_2Ph$), 4.04 (d, 2H, $CH_2CO_2CH_2Ph$), 3.81 (d, 2H, $CH_2NHBOC$), 1.40 [s, 9H, $CO_2C(CH_3)_3$].

2-[2-(tert-Butoxycarbonyl)-acetamido]-acetic acid (15a)

Benzyl-2-[2-(tert-butoxycarbonyl)-acetamido]-acetate (14; 0.57 g, 1.85 mmol) was dissolved in methanol (15 mL), and then 10% Pd/C (0.06 g) was added therein with stirring for 1 h under pressure of 40 psi of hydrogen. After the reaction is completed, Pd/C was removed by filter paper and methanol was removed by concentration under reduced pressure to obtain colorless oil-like 15a (0.38 g; 100%). $^1$H-NMR (200 MHz) (DMSO) δ: 12.60 (br, s, 1H, $CO_2H$), 8.07 (t, 1H, $CONHCH_2$), 7.00 (t, 1H, NHBOC), 3.77 (d, 2H, $CH_2CO_2H$), 3.57 (d, 2H, $CH_2NHBOC$), 1.40 [s, 9H, $CO_2C(CH_3)_3$].

Benzyl-2-(2-aminoacetamido)acetate, TFA salt (15b)

Benzyl-2-[2-(tert-butoxycarbonyl)-acetamido]-acetate (14; 0.58 g, 1.85 mmol) was dissolved in dichloromethane/trifluoroacetic acid mixture (4 ml; dichloromethane:trifluoroacetic acid=1:1) with stirring for 1 h at 0° C., and then the reaction was replaced under room temperature with continuous stirring for 1 h. After the reaction was completed, dichloromethane/trifluoroacetic acid mixture was removed by concentration under reduced pressure to obtain brown oil-like 15b (0.68 g; 100%). $^1$H-NMR (200 MHz) (DMSO) δ: 9.03 (t, 1H, CONH), 8.30 (br, s, 3H, $NH_3^+$), 7.32~7.40 (m, 5H, ArH), 5.17 (s, 2H, $COCH_2Ph$), 4.03 (d, 2H, $CH_2CO_2CH_2Ph$), 3.63 (br, s, 2H, $CH_2$).

Benzyl-2-{2-[5-(tert-butoxycarbonyl)-4-oxopentanamido]-acetamido}-acetate (16)

2-[2-(tert-butoxycarbonyl)-acetamido]-acetic acid (15a, 0.38 g, 1.85 mmol) was dissolved in DMF (15 mL), and the solution was cooled down to −10° C., added with EDC (0.40 g, 2.03 mmol) for stirring 15 min, and then added with benzyl-2-(2-aminoacetamido)acetate, TFA salt (15b, 0.68 g, 1.85 mmol) and triethylamine (0.4 mL, 2.88 mmol). Finally, the reaction was replaced under room temperature with continuous stirring for 6 h. After the reaction was completed, DMF was removed by concentration under reduced pressure. The obtained solid was dissolved in ethyl acetate (50 mL), and then the organic phase was washed by $H_2O$, 5% citric acid, $H_2O$, saturated $NaHCO_3$ and saturated NaCl solution separately, and dried over $MgSO_4$ and concentrated under reduced pressure to remove ethyl acetate to obtain brown solid product. The product was purified by silica gel column chromatography, while the proportion of eluting solution is dichloromethane:methanol=1:0, 24:1, 19:1 in order, and yellow solid product 16 (0.33 g; 42.3%) is obtained. $^1$H-NMR (200 MHz) (DMSO) δ: 8.33 (t, 1H, Gly$^4$-NH), 8.21 (t, 1H, Gly$^3$-NH), 8.06 (t, 1H, Gly$^2$-NH), 7.33-7.42 (m, 5H, ArH), 7.03 (t, 1H, Gly$^1$-NH), 5.19 (s, 2H, CO$_2$CH$_2$Ph), 3.92 (d, 2H, Gly$^4$-H), 3.76 (d, 4H, Gly$^3$ and Gly$^2$-H), 3.60 (d, 2H, Gly$^1$-H), 1.40 [s, 9H, CO$_2$C(CH$_3$)$_3$].

2-(2-{2-[2-(tert-Butoxycarbonyl)-acetamido]-acetamido}-acetamido-acetic acid (17)

Benzyl-2-{2-[5-(tert-butoxycarbonyl)-4-oxopentanamido]-acetamido}-acetate (16; 0.11 g, 0.26 mmol) was dissolved in methanol (10 mL), and then 10% Pd/C (0.02 g) was added therein with stirring for 1 h under pressure of 40 psi of hydrogen. After the reaction is completed, Pd/C was removed by filter paper and methanol was removed by concentration under reduced pressure to obtain yellow oil-like 17 (0.09 g; 100%). $^1$H-NMR (200 MHz) (DMSO) δ: 8.19 (t, 1H, Gly$^4$-NH), 8.12 (t, 1H, Gly$^3$-NH), 8.06 (t, 1H, Gly$^2$-NH), 7.03 (t, 1H, Gly$^1$-NH), 3.73~3.85 (m, 6H, Gly$^4$-, Gly$^3$- and Gly$^2$-H), 3.59 (d, 2H, Gly$^1$-H), 1.40 [s, 9H, CO$_2$C(CH$_3$)$_3$].

2-{2-[2-(2-aminoacetamido)-acetamido]-acetamido}-acetic acid (18)

2-(2-{2-[2-(tert-Butoxycarbonyl)-acetamido]-acetamido}-acetamido)-acetic acid (17; 0.09 g, 0.26mmol) was dissolved in dichloromethane/methanol mixture (5 ml; dichloromethane:methanol=1:1) and mixed with 10 equiv of Amberlyst A-21 (1 mg, 8.1 mmol) while shaking for 30 min. After filtering to remove Amberlyst A-21, the filtrate of the reaction products was concentrated under reduced pressure to afford white solid product 18 (0.07 g; 100%). $^1$H-NMR (200 MHz) (CD$_3$OD) δ: 4.10~3.85 (m, 8H, Gly$^4$-, Gly$^3$-, Gly$^2$-, and Gly$^1$-H).

Nucleic Acid Preparation

Single-stranded DNA (the 5' primer, 5'-AACACGCATAT-GTAATACGA CTCACTATAGGGATCGTCAGTGCAT-TGAG-3' [SEQ ID NO: 3]; the 3' primer, 5'-TACCCCT-TGGGGATACCACC-3' [SEQ ID NO:2]) was purchased from Purigo Biotech, Inc., Taiwan, and purified by PAGE. Both the 5' and 3' primers were used in a standard PCR reaction to amplify the double-stranded TW17 DNA (119 bp; 5'-GGTAACACGCATATGTAATACGACTCAC-TATAGGGATCGTCAGTGCATTGA GAATGTCAGT-GTCTTGCGCTGGGTTCGAGCGGTCCGTG-GTGCTGGCCCGGTGG TATCCCCAAGGGGTA-3' [SEQ ID NO:1]) from a plasmid derived from the pGEM-T vector (Promega, Madison, Wis., USA; Wang et al., unpublished results). PCR products were extracted by phenol-chloroform solutions, precipitated in the presence of ethanol, and redissolved in 50 mM KCl. The GMP-primed TW17 RNA (87-mer; 5'-GGGAUCGUCAGUGCAUUGAGAAGUG-CAGUGUCUUGCGCUGGGU UCGAGCGGUCCGUGGUGCUGGCCCGGUG-GUAUCCCCAAGGGGUA-3' [SEQ ID NO:4]) was transcribed from the PCR-amplified double-stranded TW17 DNA carrying T7 promoter sequences under the T7 RNA polymerase runoff reaction in the presence of 6.25 mM each of ATP, CTP, GTP, and UTP, 10 mM GMP (guanosine monophosphate) and with or without 5 μCi [α-$^{32}$P]UTP (Izotop, Hungary). The GMP-primed TW17 RNA transcript was separated by 8% urea PAGE (220 V, 120 min), followed by ethanol precipitation. Acquired nucleic acids were quantified by their absorption at A$_{260}$.

Nucleic Acid Radiolabeling

The TW17 RNA was body-labeled with $^{32}$P during T7 RNA polymerase runoff transcription described above. The double-stranded and single-stranded DNA molecules were $^{32}$P-labeled at their 5'-ends with the procedures following the manufacture's instruction (Promega, Madison, Wis., USA) and briefly described below. The double-stranded or single-stranded DNA (200 pmol) was dissolved in 20 μL of DEPC (diethyl dicarbonate) water, followed by the addition of 10× reaction buffer (3 μL), alkaline phosphatase (3 U), and DEPC water (4 μL). The reaction was stopped after 2 h at 37° C., and the reaction product was purified by phenol/chloroform and chloroform extractions, followed by ethanol precipitation. The 5'-OH nucleic acids were redissolved in 7 g L of DEPC water, mixed with 10× reaction buffer (1 μL), [γ-$^{32}$P]ATP (Izotop, Hungary) and T4 polynucleotide kinase (10 U; Promega, Madison, Wis., USA), and reacted for 2 h at 37° C. $^{32}$P-labeled double-stranded DNA was purified by phenol/chloroform and chloroform extractions, followed by ethanol precipitation. Single-stranded DNA with $^{32}$P-labeled 5'-end was purified by 20% urea PAGE.

Coupling 11 to the TW17 RNA for Optimization of Phosphoramidation Reactions

Please refer to FIGS. 1(A)~1(F), which show the results of optimization of phosphoramidation reactions. To make nucleic acid activated by EDC more completely, the concentration of nucleic acid is changed from 1.5 μM to 25.2 and it is discovered that there is a best yield while the concentration is 6.31 μM; the concentration of EDC is changed from 0.1 M to 1.6 M, and there is a best yield while the concentration is 0.4 M; and finally the activation time of EDC is changed from 30 min to 180 min, and 90 min is determined to have the best yield. Subsequently the concentration of imidazole is changed from 0.01 M to 1 M, and 0.1 M is determined to have the best yield; similarly the concentration of 11 dissolved in DMF is changed from 46 mM to 748 mM, and 187 mM has the best yield; in addition, the coupling time of 11 and nucleic acid is changed from 3 h to 16 h, and 3 h is determined to achieve the best yield; furthermore the reaction temperature is changed in a range of 25-50° C., and the most appropriate temperature is 41° C.; and finally the pH value of the added EPPS buffer is discussed and changed in a range of pH 6.0-9.0, and pH 8.0 can acquire the best yield.

Figure 2:
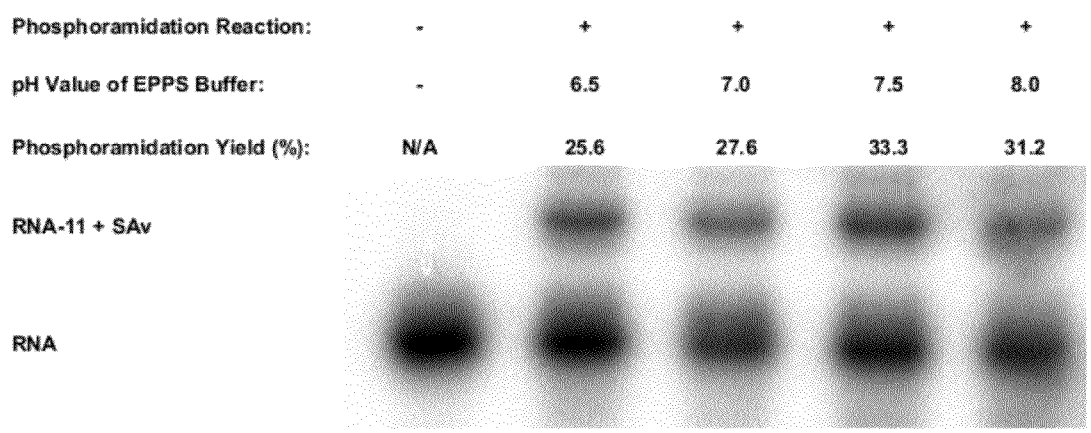
FIG. 2 shows the results of optimization of pH value of EPPS buffer for two-step phosphoramidation reaction.

Please refer to FIG. 2, which shows the results of optimization of pH value of EPPS buffer for two-step phosphoramidation reaction. The pH value is measured from pH 6.5 to pH 8.0 for two-step phosphoramidation reaction additionally, and pH 7.5 is determined to have the best yield.

Please refer to FIGS. 3(A)~3(B), which show phosphoramidation reactions of the $^{32}$P-labeled GMP-primed TW17 RNA with 11, wherein FIG. 3(A) shows results from the one-step phosphoramidation reaction, and FIG. 3(B) shows results from the two-step phosphoramidation reaction. In both figures, the top arrow indicates the location of the TW 17 RNA-11 conjugate, and the bottom arrow represents migration of the GMP-primed TW 17 RNA. The optimized one-step phosphoramidation reaction provided an excellent yield of 79% for conjugation of the TW17 RNA with 11 after 3 h reactions. Maintenance of denaturing conditions by 6.77 M urea during the phosphoramidation reaction plays a pivotal role in achieving higher yields by preventing formation of RNA secondary structures. Yields of the two-step phosphoramidation reactions for the TW17 RNA-11 conjugate preparation were consistent with expectations of lower yields than the one-step phosphoramidation reactions (52% in the presence of 6.77 M urea and 40% without 6.77 M urea). Lower yields for two-step phosphoramidation reactions are attributed to phosphorimidazolide intermediate hydrolysis during its workup step. However, similar to the one-step reactions, RNA degradation was also observed. RNA degradation was thus not caused by prolonged carbodiimide activation but rather by the nucleophile attack step or by a higher reaction temperature at 41° C.

One-Step Phosphoramidation Reactions

The standard one-step phosphoramidation reaction for RNA was carried out by dissolving the GMP-primed TW17 RNA (92 pmol) and EDC (6.52 µmol) in 20 µL urea-imidazole buffer (8 M urea, 0.1 M imidazole, pH 6.0) and activating at room temperature for 90 min, followed by the addition of 7.5 µL urea-EPPS buffer (8 M urea, 100 mM EPPS, 2 mM EDTA, pH 8.0) and 5 µL of 11 (187.2 mM in DMF) reacting at 41° C. for 3 h. The double-stranded TW17 DNA was also conjugated with 11 according to the same phosphoramidation reaction described above. For single-stranded DNA (the 3'-primer DNA), the phosphoramidation reaction was modified by dissolving single-stranded DNA (92 pmol) and EDC (6.52 µmol) in 20 µL imidazole buffer (0.1 M imidazole, pH 6.0) and activating at room temperature for 90 min, followed by the addition of 7.5 µL EPPS buffer (100 mM EPPS, 2 mM EDTA, pH 8.0) and 5 µL of 11 (187.2 mM in DMF) with subsequent reactions at 41° C. for 3 h. All resulting nucleic acid-11 conjugates were purified twice by ethanol precipitation, and their reaction yields were analyzed by SAv gel shift assay (8% urea PAGE for the TW17 DNA and RNA, and 20%/8% biphasic urea PAGE for single-stranded DNA), visualized, and quantified by an Amersham Typhoon PhosphorImager.

One-Step Phosphoramidation Reactions Applied for Preparation of Phosphoramidated DNA-11 Conjugates Please refer to FIGS. 4(A)~4(B), which show the one-step phosphoramidation reactions for the conjugations of the $^{32}$P-labeled DNA with 11, wherein FIG. 4(A) shows 8% urea PAGE for the double-stranded DNA (the TW17 DNA) conjugations, and FIG. 4(B) shows 20% urea PAGE for the single-stranded DNA (the 3'-primer) conjugations. In each figure, the top arrow indicates the location of the DNA-11 conjugate, and the bottom arrow represents migration of the DNA without phosphoramidation reactions. The one-step phosphoramidation reactions for the conjugations of either the single-stranded 3'-primer or the double-stranded TW17 DNA with 11 in the presence of 6.77 M urea offered a yield of 80% for the TW17 DNA-11 conjugate and 60% for the 3'-primer DNA-11 conjugate. These yields were comparable to the 79% yield for the TW17 RNA-11 conjugate. The addition of 6.77 M urea significantly improved the yields for the TW17 DNA-11 conjugates from 23%, without urea, to 80% in the presence of urea. These yields parallel the positive effect of urea during the phosphoramidation reactions to prepare the TW17 RNA-11 conjugates, and are consistent with the proposed function of urea to disassemble secondary structures in nucleic acids and increase the availability of terminal phosphate groups for phosphoramidation reactions. The positive effect of urea on phosphoramidation reaction yields was, however, not observed upon preparation of the 3'-primer DNA-11 conjugates. Slight deterioration of the phosphoramidation reaction yield for the 3'-primer DNA-11 conjugates was observed in the presence of urea. This finding indicates very limited secondary structure formation in a relatively small 3'-primer DNA, and adverse effects of urea on single-stranded DNA phosphoramidation reactions. In contrast to results of the TW17 RNA phosphoramidation reactions, DNA degradation was not observed during the one-step DNA phosphoramidation reactions.

Two-Step Phosphoramidation Reactions

The standard two-step phosphoramidation reaction for RNA was carried out by dissolving the GMP-primed TW17 RNA (92 pmol) and EDC (6.52 µmol) in 20 µL urea-imidazole buffer (8 M urea, 0.1 M imidazole, pH 6.0) and activating at room temperature for 90 min. The resulting 5'-phosphorimidazolide was purified by ethanol precipitation, redissolved in 27.5 µL of urea-EPPS buffer (8 M urea, 100 mM EPPS, 2 mM EDTA, pH 7.5), and added to 5 µL of 11 (187.2 mM in DMF) under reaction temperature at 41° C. for 3 h. For the single-stranded 3'-primer DNA, the two-step phosphoramidation reaction was modified by dissolving single-stranded DNA (92 pmol) and EDC (6.52 µmol in 20 µL imidazole buffer (0.1 M imidazole, pH 6.0) and activating at room temperature for 90 min. Again, the resulting 5'-phosphorimidazolides were also purified by ethanol precipitation, redissolved in 27.5 µL of EPPS buffer (100 mM EPPS, 2 mM EDTA, pH 7.5), and added to 5 µL of 11 (187.2 mM in DMF) to react at 41° C. for 3 h. The double-stranded TW17 DNA was also conjugated with 11 according to the same two-step phosphoramidation reaction for the single-stranded DNA. All acquired nucleic acid-11 conjugates were purified twice by ethanol precipitation, and their reaction yields were analyzed by SAv gel shift assay in the same urea PAGE described for one-step phosphoramidation reaction analysis, visualized, and quantified by an Amersham Typhoon PhosphorImager.

Two-Step Phosphoramidation Reactions Applied for Preparation of Phosphoramidated DNA-11 Conjugates Please refer to FIGS. 5(A)~5(B), which show the two-step phosphoramidation reactions for the conjugations of the $^{32}$P-labeled DNA with 11, wherein FIG. 5(A) shows 8% urea PAGE for the double-stranded DNA (the TW17 DNA) conjugations, and FIG. 5(B) shows 20% urea PAGE for the single-stranded DNA (the 3'-primer) conjugations. In each figure, the top arrow indicates the location of the DNA-11 conjugate, and the bottom arrow represents migration of the DNA without phosphoramidation reactions. The two-step phosphoramidation reactions for conjugation of either the 3'-primer or the TW17 DNA with 11 again provided yields lower than those for the one-step reactions. Interestingly, both phosphoramidation reactions performed better in the absence of 6.77 M urea in which the yield for the TW17 DNA-11 conjugate was 38% and that for the 3'-primer DNA-11 conjugate was 30%. The inhibitory effect of urea on phosphoramidation reactions was clearly more prominent than its beneficial effect on denaturation of nucleic acids to disrupt their secondary structures in the two-step DNA phosphoramidation reaction. DNA degradation during the two-step DNA phosphoramidation reaction was not observed.

Preparation of Nucleic Acid-1,6-Hexanediamine Conjugates

Figure 6:
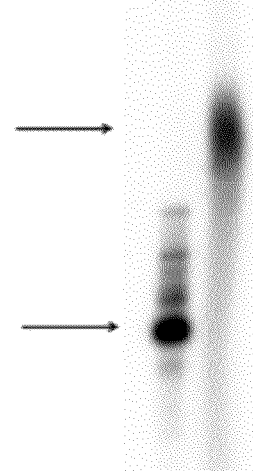
Figure 6:
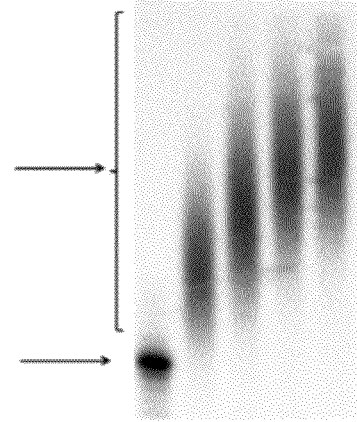
Figure 6:
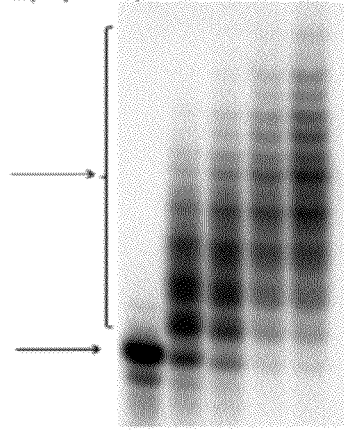

Please refer to FIGS. 6(A)~6(C), which show the phosphoramidation reactions of the $^{32}$P-labeled DNA or RNA with 1,6-hexanediamine, wherein FIG. 6(A) is for the GMP-primed TW17 RNA conjugations, FIG. 6(B) is for the doubled-stranded TW17 DNA conjugations, and FIG. 6(C) is for the single-stranded 3'-primer DNA conjugations. In each figure, the top arrow indicates location(s) of nucleic acid-1,6-hexanediamine conjugate(s), and the bottom arrow represents migration of the nucleic acid without phosphoramidation reactions. The nucleic acid-1,6-hexanediamine conjugates can serve as key intermediates for covalently linking chromophores or oligopeptides to nucleic acids. One-step phosphoramidation reactions were chosen to attain higher phosphoramidation yields for nucleic acid-1,6-hexanediamine conjugates. After 3 h phosphoramidation reaction, the yield of the TW17 RNA-1,6-hexanediamine conjugates achieves 100%, which is higher than that of the TW17 RNA-11 conjugate. Quantitative formation of the TW17 DNA-1,6-hexanediamine or the 3'-primer DNA-1,6-hexanediamine conjugates was also attained even under the conditions of reduced times for EDC activation (15 min) and for 1,6-hexanediamine coupling (10 min for both DNA molecules) in the phosphoramidation reactions. Unexpectedly, multiple conjugations of 1,6-hexanediamine to either the TW17 DNA or the 3'-primer DNA were very significant, but the multiple conjugates were never observed to produce TW17 RNA-1,6-hexanediamine conjugates. Substitutions of 1,6-hexanediamine with ethylenediamine significantly decreased phosphoramidation reaction yields for all nucleic acid conjugates (data not shown).

Preparation of the 3'-Primer DNA-Fluorescein Conjugate

The quantitative 1,6-hexanediamine-3' primer DNA conjugates were applied to conjugations with FITC through covalent thiourea linkages between newly acquired primary amines in the 5'-termini of nucleic acids and FITC. 1,6-hexanediamine-3' primer DNA conjugates are dissolved in 20 sodium carbonate buffer (0.1M, pH 9.0) to enable final DNA concentration to be 2 µM. Fluorescein isothiocyanate (FITC, Acros) is dissolved in DMSO (2.57 µM) under shading, and then 20 µL FITC solution is added into 1,6-hexanediamine-3' primer DNA conjugates solution under shading to react for 8 h in darkness. Finally the product is purified by ethanol precipitation.

Phosphoramidation Reactions for Preparation of Nucleic Acid-BSA Conjugates

Figure 7:
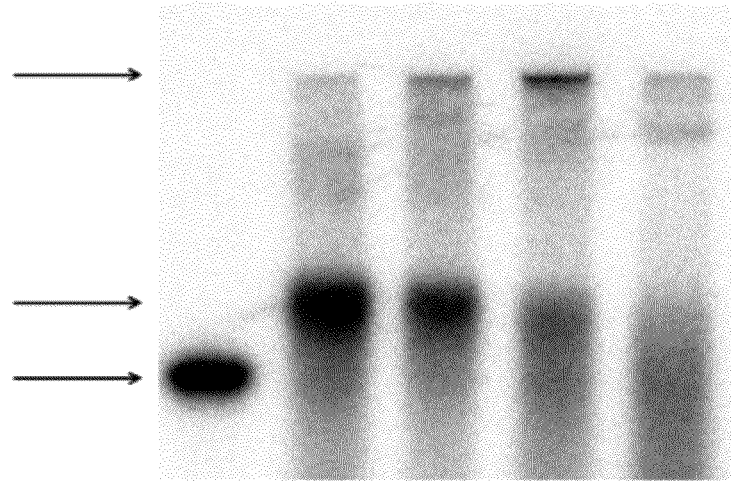
Figure 7:
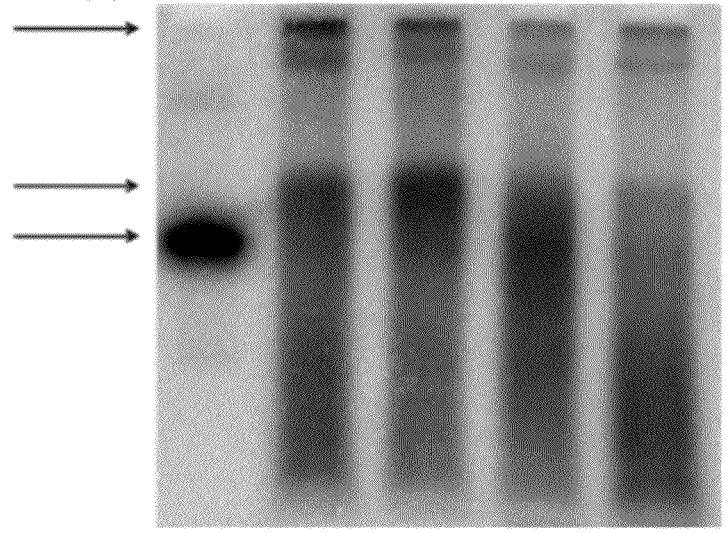
Figure 7:
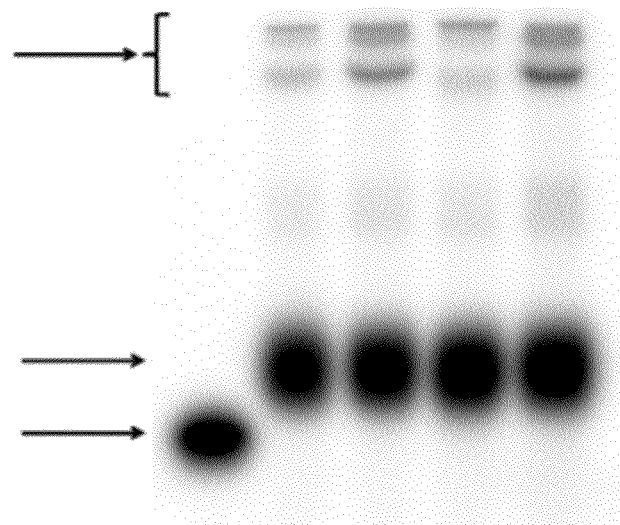
Figure 7:
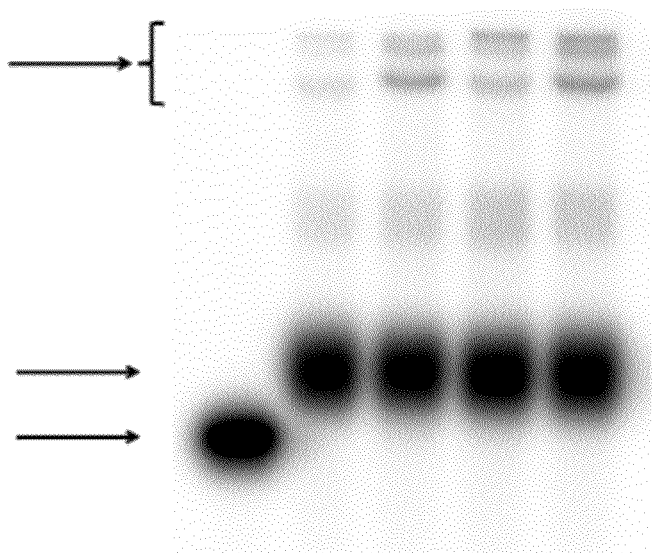

The use of phosphoramidation reactions is explored to develop a generic approach for the preparation of nucleic acid-protein conjugates. Starting with the previously prepared nucleic acid-1,6-hexanediamine conjugates (FIG. 6), they were first reacted with either DSS or DSG to effectively convert —NH2 to the NHS ester of a carboxylic acid in 5'-termini of the nucleic acids. Activated acyl group characters of NHS esters allowed easy formation of new amide linkages between nucleic acids and proteins such as BSA to acquire nucleic acid-protein conjugates. Incorporation of 3 M NaCl in coupling reactions was proposed to be indispensable to diminish electric repulsions between nucleic acids and proteins to attain higher yields for nucleic acid-protein conjugates. Therefore, the coupling reactions are performed in the presence or absence of 3 M NaCl to ascertain any benefit. Please refer to FIGS. 7(A)~7(D), which show the results of preparation of the nucleic acid-BSA conjugates. The $^{32}$P-labeled GMP-primed TW17 RNA was conjugated with 1,6-hexanediamine using the one-step phosphoramidation reaction described above, followed by reactions with DSS or DSG and finally coupled with BSA, wherein FIG. 7(A) shows the result in the absence of 3 M NaCl, FIG. 7(B) shows the result in the presence of 3 M NaCl, and the double-stranded TW17 DNA-BSA conjugates are coupled, wherein FIG. 7(C) shows the result in the absence of 3 M NaCl, and FIG. 7(D) shows the result in the presence of 3 M NaCl. The top arrow indicates the location of the TW17 RNA-BSA conjugate; the middle arrow stands for the migration of the TW17 RNA conjugates before coupling with BSA; the bottom arrow represents migration of the original GMP-primed TW17 RNA before phosphoramidation reactions. In FIG. 7(A), the yields for the TW17 RNA-BSA conjugates were only 8% using DSS linkers and 22% using DSG linkers after 2 h reactions in the absence of 3 M NaCl. Extension of the reaction time from 2 to 16 h, however, improved the yields for the TW17 RNA-BSA conjugates to 44% using DSS linkers and 34% using DSG linkers. Despite neutral pH reaction conditions (pH=7.4), RNA suffered severe degradation for both DSS and DSG linker conjugates after prolonged coupling reactions. In FIG. 7(B), preparation of the TW17 RNA-BSA conjugates after 2 h reactions in the presence of 3 M NaCl offered reasonable good yields by both DSS and DSG linkers, and was comparable to the overnight (16 h) coupling reactions in the absence of 3 M NaCl. Unexpectedly, extending the reaction time to 16 h was not necessary to improve reaction yields. The loss of the TW17 RNA-BSA conjugates during overnight reactions was observable; RNA degradation was again prevalent and more intensive during the longer reaction time. Overall, additions of 3 M NaCl when preparing the TW17 RNA-BSA conjugates, although not significantly increasing the conjugate yields, reduced the coupling time from 16 to 2 h, which is critical in preventing RNA degradation during POC preparation.

Similar coupling yields were never obtained for the preparation of the TW17 DNA-BSA conjugates. In FIG. 7(C), yields were less than 20% when using DSS or DSG linkers in the absence of 3 M NaCl. In FIG. 7(D), no improvements in yields for the coupling reactions between BSA and the TW 17 DNA derivatives were observed when the reaction times were increased from 2 to 16 h or for reactions carried out in the presence of 3 M NaCl. Such results defy the beneficial effects of prolonged reaction times and the use of 3 M NaCl to enhance the formation of DNA-alkaline phosphatase conjugates. The studies of nucleic acid-BSA conjugate preparations underscore the fundamental difference between DNA and RNA toward phosphoramidation reactions which significantly effect yields of nucleic acid-BSA conjugates.

Characteristics of Hybridization Specificity in Nucleic Acids after Phosphoramidation Reactions The effectiveness of POCs as therapeutic reagents strongly depends on intact hybridization specificity in nucleic acids after preparation. Thus, assurance of the integrity of hybridization specificity in nucleic acids after phosphoramidation reactions is essential to POC preparation reactions. For 3'-primer DNA-11 conjugate, a mixture of 3'-primer DNA-11 conjugate (1.9 µM, 10 µL) and conventional 3'-primer DNA (100 µM, 0.15 µL) substitutes for conventional 3'-primer DNA (100 µM, 0.75 µL) in the standard PCR steps, and after 25 PCR cycles, the products are obtained by phenol/chloroform extraction and ethanol precipitation, and finally analyzed by SAv gel shift assay (6%/20% biphasic urea PAGE), visualized, and quantified by an Amersham Typhoon PhosphorImager. For 3'-primer DNA-fluorescein conjugate, the same method is performed, but $^{32}$P-labeled 3'-primer DNA-11 conjugate substitutes for 3'-primer DNA-fluorescein conjugate (1.9 µM, 10 µL), and the exciting wavelength of 488 nm and absorbing wavelength of 525 nm are chosen to detect the sample signal indicating fluorescein, while the PCR products using 3'-primer DNA-fluorescein conjugate is analyzed by Amersham Typhoon PhosphorImager.

Figure 8:
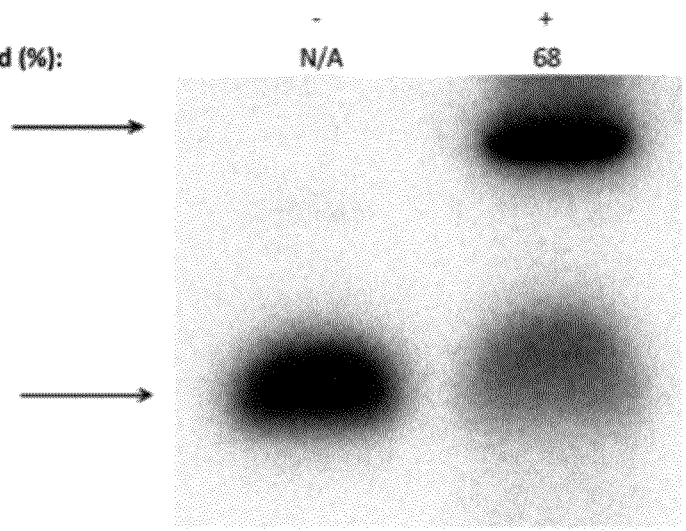
Figure 8:
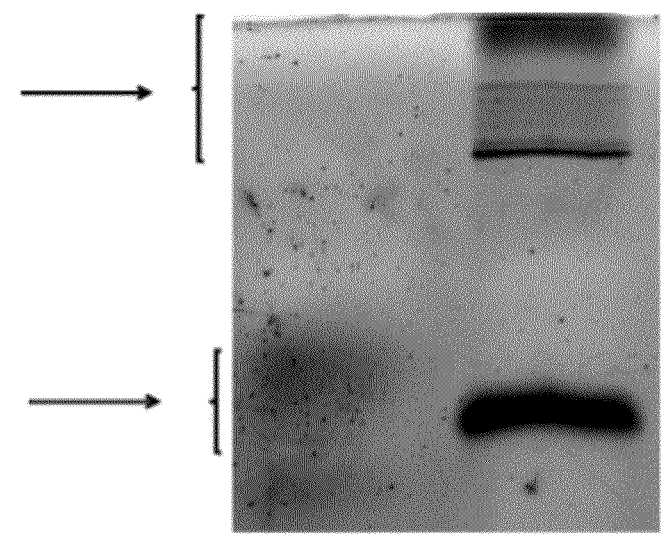

Thus the 3'-primer DNA-11 conjugate, with a known product yield, is applied to PCR reactions to clearly demonstrate intact hybridization specificity. Please refer to FIGS. 8(A)~8(B), which show the results of phosphoramidation-prepared 3'-primer DNA applied to PCR reactions, wherein FIG. 8(A) shows the result of using 3'-primer DNA-11 conjugate, and FIG. 8(B) shows the result of using 3'-primer DNA-fluorescein conjugate. In FIG. 8(A), the results from the PCR reaction indicated that 68% of the radiolabeled 3'-primer DNA was incorporated into the PCR DNA product. As the yield for the 3'-primer DNA-11 conjugate preparation, in the absence of 6.77 M urea, was 69% (FIG. 4(B)), it is concluded that all of the phosphoramidation-prepared 3'-primer DNA-11 conjugates had effectively hybridized with the provided DNA template to produce the desired DNA product. In FIG. 8(B), the results from the PCR reaction indicated that 30% of the 3'-primer DNA-fluorescein conjugate was incorporated into the PCR DNA product. It is known that the yield for 3'-primer DNA-fluorescein conjugate is almost 100% in the previous experiment, and therefore the reason of changes of PCR amplification efficiency might be attributed to the multiple conjugations from phosphoramidation reactions.

Preparation of Nucleic Acid-Tetraglycine (18) Conjugates

Figure 3:
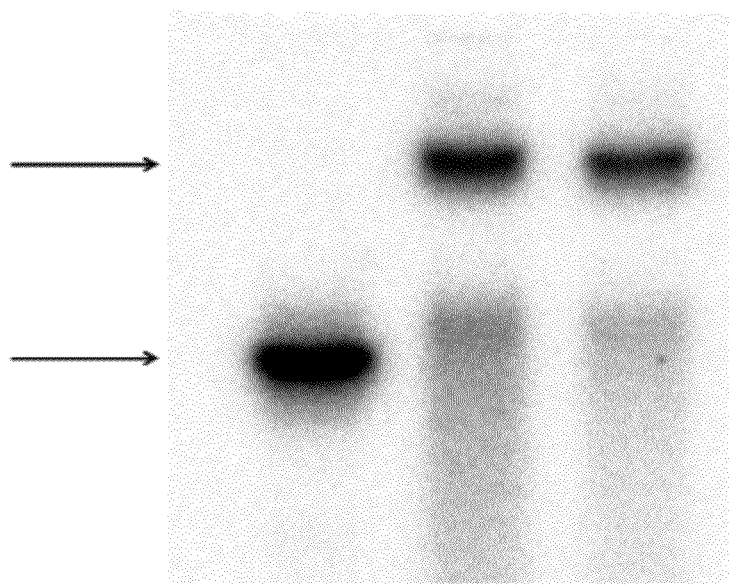
Figure 3:
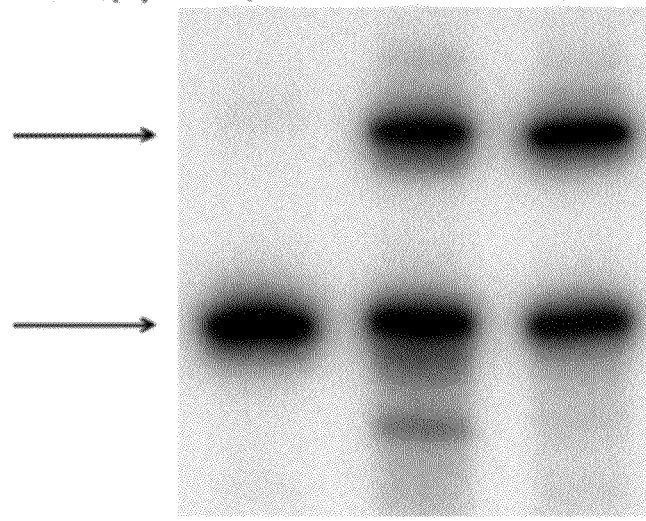
Figure 4:
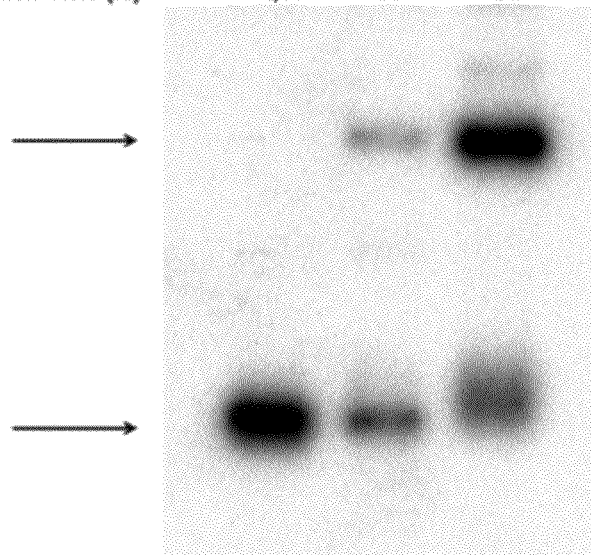
Figure 4:
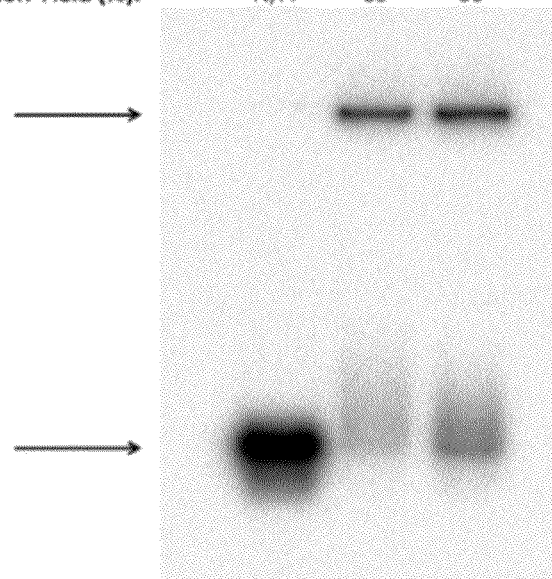
Figure 5:
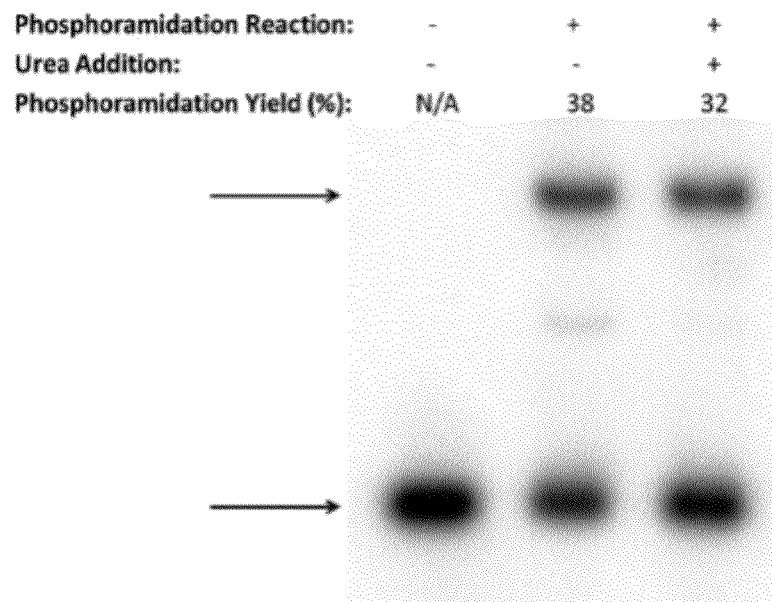
Figure 5:
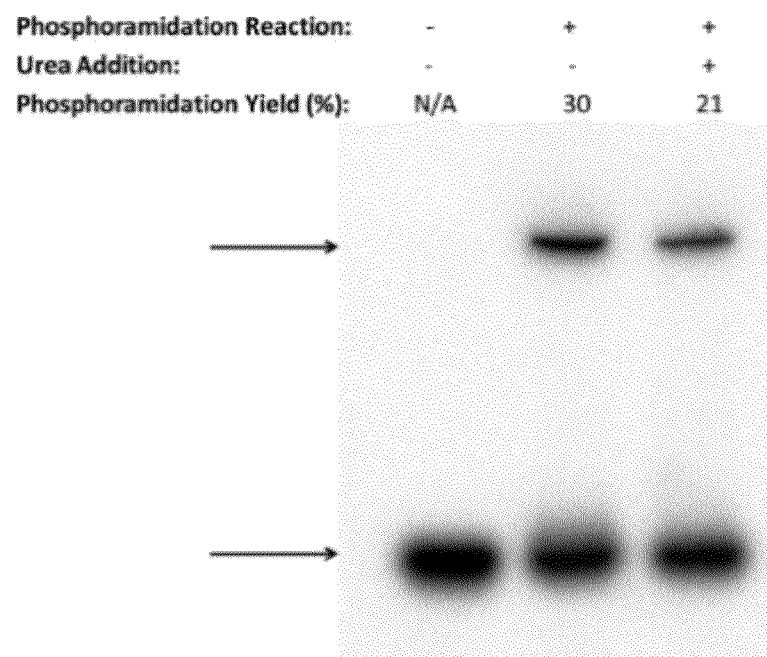

Understanding the basic chemistry for nucleic acid phosphoramidation provided essential information to develop appropriate and simple protocols for POC preparation. The results initially implied that one-step phosphoramidation reactions were superior in preparing POCs because of their better reaction yields (FIGS. 3-5). Phosphoramidation reactions of DNA with 1,6-hexanediamine, however, revealed that the one-step approach was too reactive to produce multiple conjugations in DNA molecules and had adverse effects on hybridization specificity (FIGS. 6(B)-6(C)). In addition, generic one-step nucleic acid phosphoramidation reactions have restrictions on nucleophile carbodiimide-sensitive functionalities, which demand the use of carboxyl-protected peptides to participate in one-step nucleic acid phosphoramidation reactions for POC preparation. Two-step phosphoramidation is applied in this reaction to protect the integrity of hybridization specificity in nucleic acid moieties and avoid the reaction between EDC and the peptides.

Figure 9:
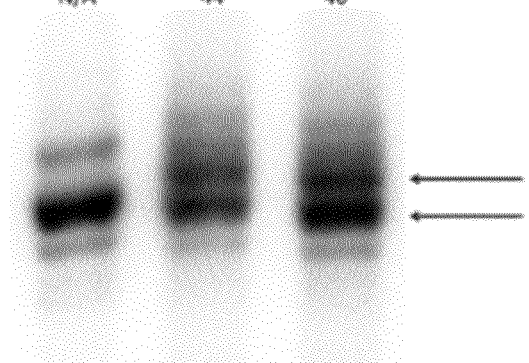
Figure 9:
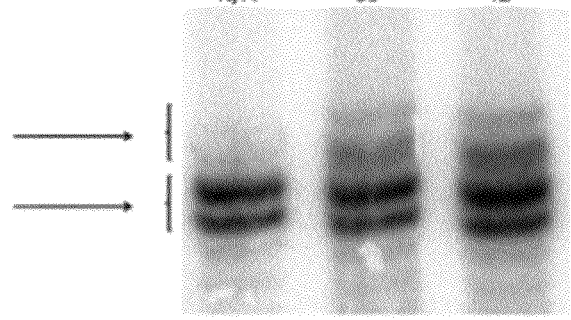
Figure 9:
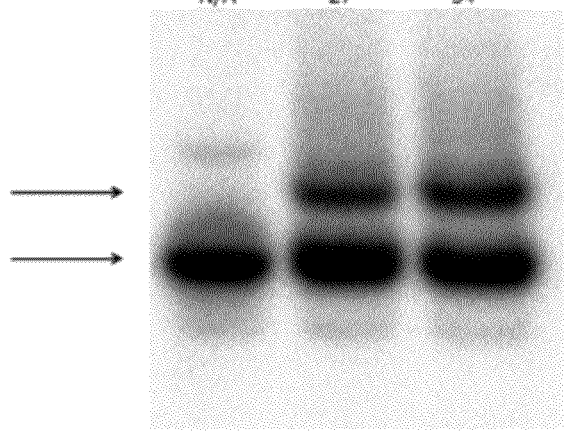

Tetraglycine (18) is synthesized as a model peptide and allowed to react with nucleic acids by two-step phosphoramidation reactions. Please refer to FIGS. 9(A)-9(C), which show the phosphoramidation reactions of the $^{32}$P-labeled DNA or RNA with tetraglycine (18) to prepare nucleic acid-tetraglycine conjugates, wherein FIG. 9(A) is for the GMP-primed TW 17 RNA conjugations, FIG. 9(B) is for the doubled-stranded TW17 DNA conjugations, and FIG. 9(C) is for the single-stranded 3'-primer DNA conjugations. In each figure, the top arrow indicates the location of the nucleic acid-18 conjugate, and the bottom arrow represents migration of the original nucleic acid. Consistent with the previous studies of nucleic acid conjugations with 11 by two-step phosphoramidation reactions, the acquired nucleic acid-18 conjugates after 3 h of coupling reactions with nucleophile 18 had the following yields: the TW17 RNA-18 conjugate of 44%, the TW17 DNA-18 conjugate of 39%, and the 3'-primer DNA-18 conjugate of 27%. The molecular mass difference between two DNA strands in the double-stranded TW17 DNA, which is over 500 Da, contributes to the observation of a dual DNA signal before and after the phosphoramidation reaction (FIG. 9(B); calculated molecular mass: the positive strand of the TW17 DNA, 36 963.8 g/mol; the negative strand of the TW17 DNA, 36 448.6 g/mol). The product yields are comparable to the two-step phosphoramidation reactions for nucleic acid-11 conjugate preparation. Extending the reaction time for 18 to overnight (16 h) improved DNA-18 conjugate yields, but not for the TW17 RNA-18 conjugate. A lower yield for the TW17 RNA-18 conjugate after the overnight coupling reaction could be attributed to instability of RNA during a prolonged coupling period. However, 3 h of reactions with peptide nucleophiles in two-step nucleic acid phosphoramidation is enough to prepare suitable amounts of POCs. No multiple conjugations were observed in any nucleic acid-18 conjugates, implying the integrity of hybridization specificity in nucleic acid moieties. These results clearly validate the two-step phosphoramidation reaction to prepare appropriate POCs for medical applications. Yields for all phosphoramidation reactions are provided in Table 1.

TABLE 1

Yields for Nucleic Acid Conjugates Directly or Indirectly Prepared from Phosphoramidation Reactions

| Nucleophiles | TW17 RNA | TW17 DNA | 3' primer DNA |
| --- | --- | --- | --- |
| 11 (one-step phosphoramidation) | 70%$^a$, 79%$^b$ | 23%$^a$, 80%$^b$ | 69%$^a$, 60%$^b$ |
| 11 (two-step phosphoramidation) | 40%$^a$, 52%$^b$ | 38%$^a$, 32%$^b$ | 30%$^a$, 21%$^b$ |
| 18 (two-step phosphoramidation) | 44%$^c$, 40%$^d$ | 39%$^c$, 42%$^d$ | 27%$^c$, 34%$^d$ |
| 1,6-hexanediamine (one-step phosphoramidation) | 100% | 100%$^e$ | 100%$^e$ |
| BSA (one-step phosphoramidation)$^f$ | 8%$^g$, 44%$^h$, 45%$^i$, 26%$^j$ | 5%$^g$, 5%$^h$, 2%$^i$, 4%$^j$ | N/A$^k$ |
| BSA (one-step phosphoramidation)$^l$ | 22%$^g$, 34%$^h$, 32%$^i$, 44%$^j$ | 10%$^g$, 12%$^h$, 5%$^i$, 7%$^j$ | N/A$^k$ |

$^a$In the absence of 6.77M urea.
$^b$In the presence of 6.77M urea.
$^c$For a 3 h phosphoramidation reaction.
$^d$For a 16 h phosphoramidation reaction.
$^e$Under the conditions of 15 min EDC activation and 20 min 1,6-hexanediamine coupling reactions.
$^f$Using DSS as the linker.
$^g$For a 2 h coupling reaction with BSA in the absence of 3M NaCl.
$^h$For a 16 h coupling reaction with BSA in the absence of 3M NaCl.
$^i$For a 2 h coupling reaction with BSA in the presence of 3M NaCl.
$^j$For a 16 h coupling reaction with BSA in the presence of 3M NaCl.
$^k$Not analyzed.
$^l$Using DSG as the linker.

The Effects of Surfactant on the Yields of Phosphoramidation Reactions

Urea plays a role of surfactant in the phosphoramidation reaction, and is 32.4% by weight in standard phosphoramidation reaction. Since urea has the character of nucleophile and will affect the yield of phosphoramidation reaction, it substitutes for Tween 20, Triton X-100, PEG 6000, PEG 8000 or glycerol in the phosphoramidation reaction, and two-step phosphoramidation reaction is performed by standard nucleic acid and 11 under the conditions of 15%, 20%, 25% and 32% surfactant respectively. Finally the product is purified by ethanol precipitation and analyzed by the urea PAGE-SAv gel shift assay and Typhoon PhosphorImager.

Figure 10:
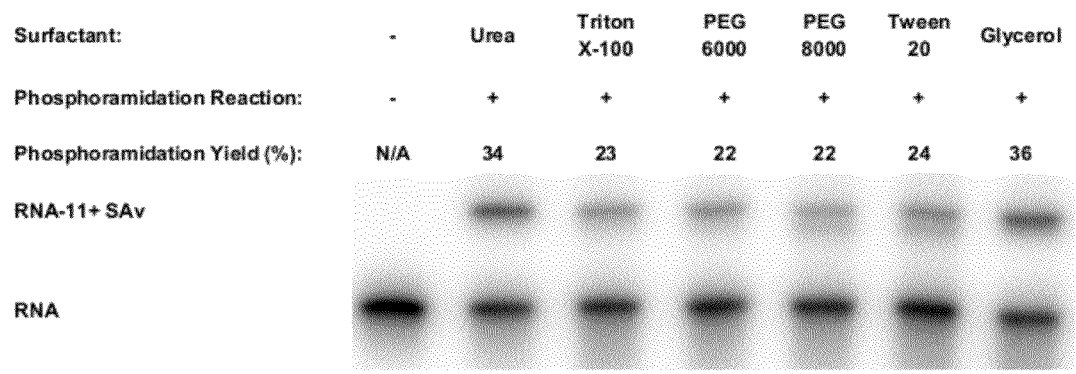
Figure 10:
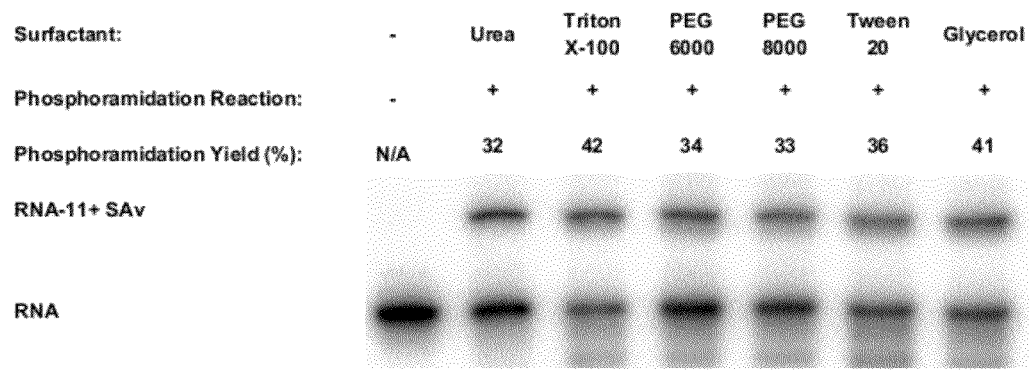
Figure 10:
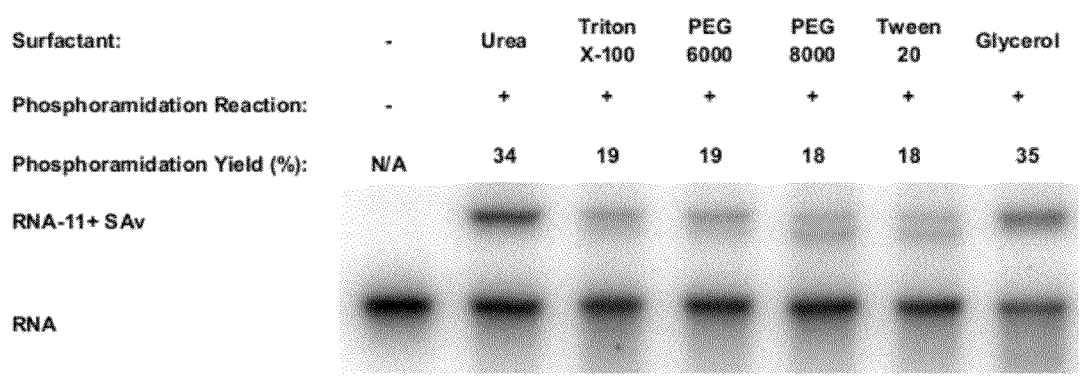
Figure 10:
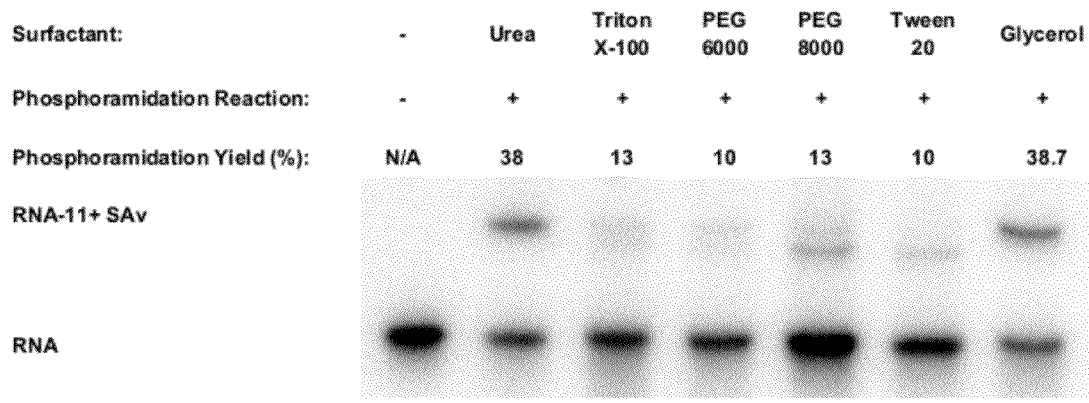

Please refer to FIGS. 10(A)-10(D), which show the effects of the type and concentration of surfactant on the yields of two-step phosphoramidation reactions, wherein FIG. 10(A) shows the effect under 15% surfactant, FIG. 10(B) shows the effect under 20% surfactant, FIG. 10(C) shows the effect under 25% surfactant, and FIG. 10(D) shows the effect under 32% surfactant. It can be seen that 20% surfactant has higher yields than those of other concentrations, wherein the yields of Triton X-100 and glycerol are higher than that of urea by around 10%. In the conditions of 15% and 25% surfactant (FIGS. 10(A) and 10(C)), except glycerol can retain the same yield as urea, other surfactants, on the contrary, cause decreasing yields. In FIG. 10(D), under the condition of 32% surfactant, glycerol retains the same yield as urea, but other surfactants cause much obvious decreasing yields than those under the conditions of 15% and 25% surfactant. Therefore an appropriate amount of surfactant indeed increases the yield of two-step phosphoramidation reaction, but an excess of surfactant will decrease the yield of phosphoramidation reaction.

Embodiments

1. A method for conjugating a nucleic acid with a molecule, comprising steps of:

(a) reacting the nucleic acid having a 5'-monophosphate with an activating agent in a first buffer to form a solution;

(b) mixing an alcohol with the solution formed in the step (a) to obtain an intermediate; and (c) dissolving the intermediate in a second buffer containing an ethylenediaminetetraacetic acid (EDTA) and adding a nucleophile thereinto to react the intermediate with the nucleophile.

2. The method of Embodiment 1, wherein: the nucleic acid having the 5'-monophosphate has a concentration ranged from 3.2 to 12.6 µM;

the activating agent is an 1-(3-dimethylaminopropyl)-1-ethylcarbondiimide hydrochloride (EDC);

the activating agent has a concentration ranged from 0.1 to 1.2 M;

the first buffer is an imidazole buffer;

the first buffer has a concentration ranged from 0.1 to 1 M;

the step (a) has a reaction time ranged from 20 to 180 min;

the intermediate is formed by an ethanol precipitation in the step (b);

the intermediate includes 5'-phosphorimidazolide;

the second buffer is an 3-[4-(2-hydroxyethyl)-1-piperazinyl]propanesulfonic acid (EPPS) buffer having a pH value ranged from 7.0 to 8.0;

the nucleophile has one of concentrations larger than and equal to 187 mM; and the molecule comprises one selected from a group consisting of a biotin derivative, a fluorescein, a developer, a protein and a peptide.

3. The method of any one of Embodiments 1-2, wherein the nucleic acid is one selected from a group consisting of an RNA molecule, a double-stranded DNA molecule and a single-stranded DNA molecule.

4. The method of any one of Embodiments 1-3, wherein when the nucleic acid is RNA, each of the first buffer and the second buffer further contains an 8 M urea.

5. The method of any one of Embodiments 1-4, wherein the nucleophile is a linker linking the nucleic acid and the molecule and including one of 1,6-hexanediamine and ethylenediamine.

6. The method of any one of Embodiments 1-5, wherein the nucleophile includes the molecule having at least an amino group.

7. The method of any one of Embodiments 1-6, wherein the nucleophile includes the molecule having one amino group.

8. The method of any one of Embodiments 1-7, wherein the molecule having the amino group comprises one selected from a group consisting of a biotin derivative, a developer, a protein and a peptide.

9. The method of any one of Embodiments 1-8, wherein the nucleic acid retains a characteristic of base pairing.

10. A method for conjugating a nucleic acid with a molecule, comprising steps of:

(a) reacting the nucleic acid having a 5'-monophosphate with an activating agent in a first buffer to form a solution; and (b) adding a second buffer containing an ethylenediaminetetraacetic acid (EDTA) and a nucleophile into the solution.

11. The method of Embodiment 10, wherein: the nucleic acid having the 5'-monophosphate has a concentration ranged from 3.2 to 12.6 µM;

the activating agent is an 1-(3-dimethylaminopropyl)-1-ethylcarbondiimide hydrochloride (EDC);

the activating agent has a concentration ranged from 0.1 to 1.2 M;

the first buffer is an imidazole buffer; the first buffer has a concentration ranged from 0.1 to 1 M;

the step (a) has a reaction time ranged from 20 to 180 min;

the second buffer is an 3-[4-(2-hydroxyethyl)-1-piperazinyl]propanesulfonic acid (EPPS) buffer having a pH value ranged from 8.0 to 8.5;

the nucleophile has one of concentrations larger than and equal to 187 mM;

the step (b) further includes a sub-step of forming a nucleic acid-molecule conjugate;

the method further comprises a step (c) of purifying the nucleic acid-molecule conjugate by an alcohol precipitation process; and the molecule comprises one selected from a group consisting of a biotin derivative, a fluorescein, a developer, a protein and a peptide.

12. The method of any one of Embodiments 10-11, wherein the nucleic acid is one selected from a group consisting of an RNA molecule, a double-stranded DNA molecule and a single-stranded DNA molecule.

13. The method of any one of Embodiments 10-12, wherein when the nucleic acid is one of the RNA and the double-stranded DNA, each of the first buffer and the second buffer further contains an 8 M urea.

14. The method of any one of Embodiments 10-13, wherein when the nucleic acid is the RNA, the nucleophile is a linker linking the nucleic acid and the molecule and including one of an 1,6-hexanediamine and an ethylenediamine.

15. The method of any one of Embodiments 10-14, wherein the nucleophile is the molecule having at least an amino group.

16. The method of any one of Embodiments 10-15, wherein the nucleophile is the molecule having one amino group.

17. The method of any one of Embodiments 10-16, wherein the molecule having the amino group comprises one of a biotin derivative and a developer having the amino group.

18. The method of any one of Embodiments 10-17, wherein the nucleic acid retains a characteristic of base pairing.

19. A process being one selected from a group consisting of RNA interference, gene silencing, gene therapy, nucleic acid/protein quantification and detection of in vivo protein-nucleic acid interaction, performed by using the method of any one of Embodiments 1-18.

20. A compound having a structure of:

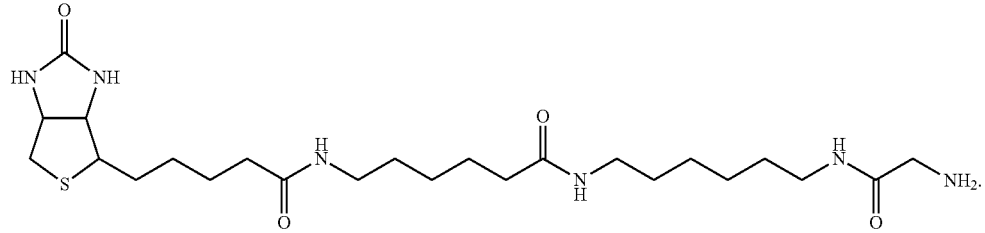 [SMILES: NCC(=O)NCCCCCCNC(=O)CCCCCNC(=O)CCCCC1SCC2NC(=O)NC21]

Based on the above, the present invention effectively solves the problems and drawbacks in the prior art, and thus it fits the demand of the industries and is industrially valuable.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

(b) mixing an alcohol with the solution formed in the step (a) to obtain an intermediate; and
(c) carrying out one of steps (c1) to (c2)
(c1) dissolving the intermediate in a second buffer containing an ethylenediaminetetraacetic acid (EDTA) and adding a first nucleophile thereinto to react the intermediate with the first nucleophile, wherein the first nucleophile includes the molecule; and
(c2) providing the molecule, dissolving the intermediate in the second buffer containing the EDTA and adding a second nucleophile thereinto to react the intermediate with the second nucleophile, and then reacting the second nucleophile with the molecule.

What is claimed is:

1. A method for conjugating a nucleic acid with a molecule, comprising steps of:
(a) reacting the nucleic acid having a 5'-monophosphate with an activating agent in a first buffer to form a solution;

2. The method as claimed in claim 1, wherein:
the nucleic acid having the 5'-monophosphate has a concentration ranged from 3.2 to 12.6 µM;
the activating agent is an 1-(3-dimethylaminopropyl)-1-ethylcarbondiimide hydrochloride (EDC);

the activating agent has a concentration ranged from 0.1 to 1.2 M;
the first buffer is an imidazole buffer;
the first buffer has a concentration ranged from 0.1 to 1 M;
the step (a) has a reaction time ranged from 20 to 180 min;
the intermediate is formed by an ethanol precipitation in the step (b);
the intermediate includes 5'-phosphorimidazolide;
the second buffer is an 3-[4-(2-hydroxyethyl)-1-piperazinyl]propanesulfonic acid (EPPS) buffer having a pH value ranged from 7.0 to 8.0;
each of the first and the second nucleophiles has one of concentrations larger than and equal to 187 mM; and
the molecule comprises one selected from a group consisting of a biotin derivative, a fluorescein, a developer, a protein and a peptide.

3. The method as claimed in claim 1, wherein the nucleic acid is one selected from a group consisting of an RNA molecule, a double-stranded DNA molecule and a single-stranded DNA molecule.

4. The method as claimed in claim 3, wherein when the nucleic acid is RNA, each of the first buffer and the second buffer further contains an 8 M urea.

5. The method as claimed in claim 4, wherein each of the first and the second nucleophiles is a linker linking the nucleic acid and the molecule and including one of 1,6-hexanediamine and ethylenediamine.

6. The method as claimed in claim 1, wherein the molecule has at least an amino group.

7. The method as claimed in claim 6, wherein the molecule has one amino group.

8. The method as claimed in claim 6, wherein the molecule having the amino group comprises one selected from a group consisting of a biotin derivative, a developer, a protein and a peptide.

9. The method as claimed in claim 7, wherein the nucleic acid retains a characteristic of correct base pairing.

* * * * *

SEQUENCE LISTING

```
<160> NUMBER OF SEQ ID NOS: 4

<210> SEQ ID NO 1
<211> LENGTH: 119
<212> TYPE: DNA
<213> ORGANISM: Artificial Sequence
<220> FEATURE:
<223> OTHER INFORMATION: TW17 DNA

<400> SEQUENCE: 1
ggtaacacgc atatgtaata cgactcacta tagggatcgt cagtgcattg agaatgtcag      60
tgtcttgcgc tgggttcgag cggtccgtgg tgctggcccg gtggtatccc caagggta      119

<210> SEQ ID NO 2
<211> LENGTH: 20
<212> TYPE: DNA
<213> ORGANISM: Artificial Sequence
<220> FEATURE:
<223> OTHER INFORMATION: TW17 DNA 3' primer

<400> SEQUENCE: 2 tacccttgg ggataccacc                                                   20

<210> SEQ ID NO 3
<211> LENGTH: 49
<212> TYPE: DNA
<213> ORGANISM: Artificial Sequence
<220> FEATURE:
<223> OTHER INFORMATION: TW17 DNA 5' primer

<400> SEQUENCE: 3
aacacgcata tgtaatacga ctcactatag ggatcgtcag tgcattgag                  49

<210> SEQ ID NO 4
<211> LENGTH: 87
<212> TYPE: RNA
<213> ORGANISM: Artificial Sequence
<220> FEATURE:
<223> OTHER INFORMATION: TW17 RNA

<400> SEQUENCE: 4
gggaucguca gugcauugag aagugcagug ucuugcgcug gguucgagcg guccguggug      60
cuggcccggu gguaucccca aggggua                                          87
```